United States Patent
Iida et al.

(10) Patent No.: US 10,270,035 B2
(45) Date of Patent: Apr. 23, 2019

(54) POLYMER, COMPOSITION FOR ORGANIC ELECTROLUMINESCENT ELEMENT, ORGANIC ELECTROLUMINESCENT ELEMENT, ORGANIC EL DISPLAY DEVICE, AND ORGANIC EL LIGHTING DEVICE

(71) Applicant: Mitsubishi Chemical Corporation, Chiyoda-ku (JP)

(72) Inventors: Koichiro Iida, Kanagawa (JP); Yanjun Li, Kanagawa (JP); Tomokazu Umemoto, Kanagawa (JP); Qi Gao, Kanagawa (JP); Hideki Goromaru, Kanagawa (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 149 days.

(21) Appl. No.: 15/252,427

(22) Filed: Aug. 31, 2016

(65) Prior Publication Data
US 2016/0372676 A1 Dec. 22, 2016

Related U.S. Application Data

(63) Continuation of application No. PCT/JP2015/056094, filed on Mar. 2, 2015.

(30) Foreign Application Priority Data

Mar. 3, 2014 (JP) .................. 2014-040769

(51) Int. Cl.
| | |
|---|---|
| H01L 51/54 | (2006.01) |
| H01L 51/00 | (2006.01) |
| C08G 73/02 | (2006.01) |
| C07C 13/66 | (2006.01) |
| C07C 25/02 | (2006.01) |
| C07C 25/22 | (2006.01) |
| C07C 39/17 | (2006.01) |
| C07C 211/45 | (2006.01) |
| C07C 309/00 | (2006.01) |
| C07F 5/04 | (2006.01) |
| H01L 51/50 | (2006.01) |

(52) U.S. Cl.
CPC .......... *H01L 51/0039* (2013.01); *C07C 13/66* (2013.01); *C07C 25/02* (2013.01); *C07C 25/22* (2013.01); *C07C 39/17* (2013.01); *C07C 211/45* (2013.01); *C07C 309/00* (2013.01); *C07F 5/04* (2013.01); *C08G 73/02* (2013.01); *H01L 51/0043* (2013.01); *C07C 2602/06* (2017.05); *C07C 2603/08* (2017.05); *C07C 2603/50* (2017.05); *H01L 51/0003* (2013.01); *H01L 51/008* (2013.01); *H01L 51/0058* (2013.01); *H01L 51/0059* (2013.01); *H01L 51/0067* (2013.01); *H01L 51/0072* (2013.01); *H01L 51/0081* (2013.01); *H01L 51/0085* (2013.01); *H01L 51/5056* (2013.01); *H01L 51/5088* (2013.01)

(58) Field of Classification Search
CPC ......... C07C 25/00; C07C 25/02; C07C 25/22; C07C 13/66; C07C 39/17; C07C 211/45; C07C 309/00; C07C 2102/06; C07C 2103/08; C07C 2103/50; C08G 73/02; C07F 5/04; H01L 51/0003; H01L 51/0032; H01L 51/0039; H01L 51/0043; H01L 51/0058; H01L 51/0059; H01L 51/0067; H01L 51/0072; H01L 51/008; H01L 51/0081; H01L 51/0085; H01L 51/50; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 2011/0042661 A1* | 2/2011 | Endo | C08G 61/12 257/40 |
| 2011/0108814 A1 | 5/2011 | Iida et al. | |
| 2011/0114926 A1 | 5/2011 | Okabe et al. | |
| 2012/0256537 A1 | 10/2012 | Nakatani et al. | |
| 2012/0326140 A1 | 12/2012 | Fukushima et al. | |
| 2013/0020562 A1 | 1/2013 | Iida et al. | |
| 2013/0200337 A1 | 8/2013 | Iida et al. | |

(Continued)

FOREIGN PATENT DOCUMENTS

| | | |
|---|---|---|
| CN | 101945925 | 1/2011 |
| CN | 101981086 A | 2/2011 |
| CN | 102106017 A | 6/2011 |

(Continued)

OTHER PUBLICATIONS

Combined Chinese Office Action and Search Report dated Mar. 7, 2018 in corresponding Patent Application No. 201580011526.2 (with English Translation) citing documents AO, AP and AX therein, 7 pages.

(Continued)

*Primary Examiner* — Andrew K Bohaty
(74) *Attorney, Agent, or Firm* — Oblon, McClelland, Maier & Neustadt, L.L.P.

(57) ABSTRACT

The object of the present invention is to provide a polymer capable of being insolubilized at a low temperature in a short time, having a high hole injecting and transporting ability and a high durability, and a composition for organic electroluminescent element comprising the polymer. The polymer of the present invention comprises a specific crosslinkable group.

12 Claims, 1 Drawing Sheet

(56) References Cited

U.S. PATENT DOCUMENTS

2015/0102334 A1  4/2015  Iida et al.

FOREIGN PATENT DOCUMENTS

| | | |
|---|---|---|
| CN | 102791768 | 11/2012 |
| EP | 2 315 291 A1 | 4/2011 |
| JP | 2004-64023 A | 2/2004 |
| JP | 2011-184684 A | 9/2011 |
| JP | 2013-170228 A | 9/2013 |
| JP | 2014-1349 A | 1/2014 |
| WO | WO 2009/123269 A1 | 10/2009 |
| WO | WO 2011/078387 A1 | 6/2011 |
| WO | WO 2011/093428 A1 | 8/2011 |
| WO | WO-2011099531 A1 * | 8/2011 ........... C08G 73/026 |
| WO | WO 2013/191137 A1 | 12/2013 |

OTHER PUBLICATIONS

Reuben D. Rieke et. al., "Ring Strain Effects. III. Reduction and Oxidation Potential Shifts," Journal of American Chemical Society, Apr. 21, 1971, pp. 1962-1967.

International Search Report dated Mar. 24, 2015 in PCT/JP2015/056094 (with English translation).

Extended European Search Report dated Feb. 1, 2017 in Patent Application No. 15758310.5.

Japanese Office Action dated Aug. 26, 2018 in Japanese Patent Application No. 2016-506482 (with unedited computer generated English translation), 6 pages.

Office Action in corresponding Chinese Patent Application No. 201580011526.2, dated Dec. 14, 2018. (w/English Translation).

Office Action in corresponding Taiwanese Patent Application No. 104106734, dated Dec. 5, 2018. (w/English Translation).

* cited by examiner

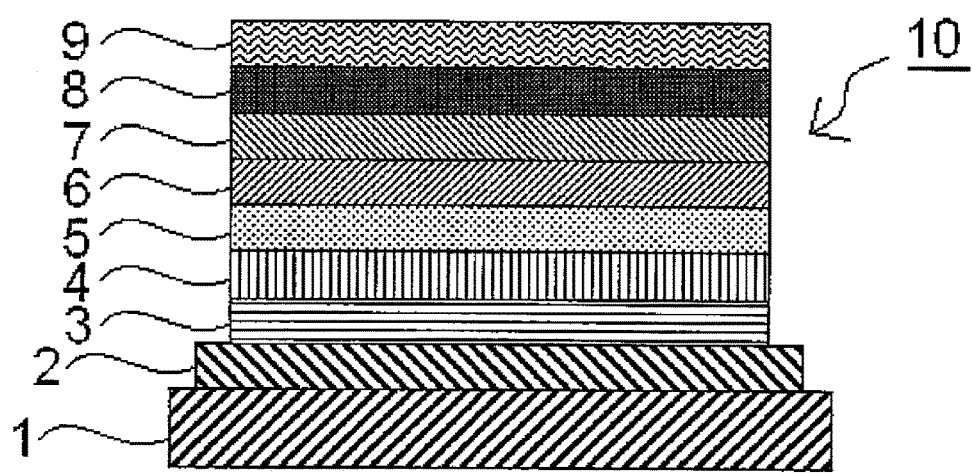

POLYMER, COMPOSITION FOR ORGANIC ELECTROLUMINESCENT ELEMENT, ORGANIC ELECTROLUMINESCENT ELEMENT, ORGANIC EL DISPLAY DEVICE, AND ORGANIC EL LIGHTING DEVICE

TECHNICAL FIELD

The present invention relates to a polymer, particularly to a polymer useful as a hole injection layer and a hole transport layer of organic electroluminescent element, and to a composition for organic electroluminescent element containing the polymer. The invention also relates to organic EL (Electro Luminescence) display device and organic EL lighting device which include such organic electroluminescent element.

BACKGROUND ART

A vacuum vapor deposition method and a wet film formation method are methods used to form organic layers of an organic electroluminescent element. For its ability to easily achieve lamination, the vacuum vapor deposition method is advantageous in terms of improving charge injection from an anode and/or a cathode, and easily trapping excitons in the light-emitting layer. On the other hand, the wet film formation method does not require the vacuum process, and can easily achieve large areas. Another advantage is that the wet film formation method, with the use of a coating liquid prepared by mixing a plurality of materials having various different functions, can easily form a layer containing different materials with different functions. However, because lamination is difficult to achieve with the wet film formation method, the wet film formation method is inferior in terms of drive stability compared to elements formed by the vacuum vapor deposition method, and, with a few exceptions, has not reached a practical level.

In order to achieve lamination by the wet film formation method, there accordingly is a need for a charge-transporting polymer having a crosslinkable group that becomes insolubilized after being coated. There is an ongoing development of such charge-transporting polymers. Specifically, PTL 1 to PTL 4 disclose polymers in which benzocyclobutene, which provides desirable durability, is contained as a crosslinkable group, and an arylamine structure, which provides desirable transporting ability, is contained as a charge-transporting moiety.

CITATION LIST

Patent Literature

PTL 1: WO2009/123269
PTL 2: WO2011/078387
PTL 3: WO2011/093428
PTL 4: WO2013/191137

SUMMARY OF INVENTION

Technical Problem

Studies by the present inventors have revealed a problem that a large energy is needed to insolubilize the benzocyclobutene-containing polymers described in PTL 1 to PTL 4, and that this requires long, high-temperature firing. Specifically, it has been found that substrates, dividing walls, insulating films, and TFTs and other members of display devices need to have high heat resistance, and that elements can be produced only in small quantities because of the long firing time.

It is accordingly an object of the present invention to provide a polymer that can be insolubilized at a low temperature in a short time period, and that has a high hole injecting and transporting ability, and high durability, and a composition for organic electroluminescent element containing the polymer. The present invention is also intended to provide an easy-to-produce organic electroluminescent element that has high luminance and a long drive lifetime.

Solution to Problem

The present inventors conducted intensive studies, and found that the foregoing problems can be solved with the use of a polymer having a specific crosslinkable group. The present invention was completed on the basis of this finding.

That is, the present invention has the following constitutions [1] to [12].

[1] A polymer having a crosslinkable group represented by the following formula (1):

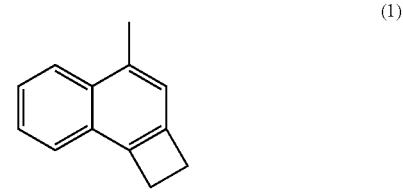

wherein the 1,2-dihydrocyclobuta[a]naphthalene ring may have a substituent.

[2] The polymer according to the [1] above, which comprises a repeating unit represented by the following formula (2):

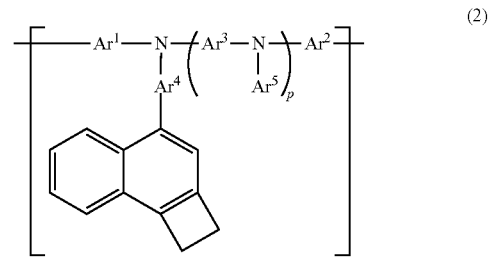

wherein p represents an integer of 0 to 3, $Ar^1$ and $Ar^2$ each independently represent a direct bond, an aromatic hydrocarbon group that may have a substituent, or an aromatic heterocyclic group that may have a substituent, $Ar^3$ to $Ar^5$ each independently represent an aromatic hydrocarbon group that may have a substituent, or an aromatic heterocyclic group that may have a substituent, and the $Ar^1$ and $Ar^2$ are not direct bonds at the same time.

[3] The polymer according to the [1] above, which comprises a repeating unit represented by the following formula (3):

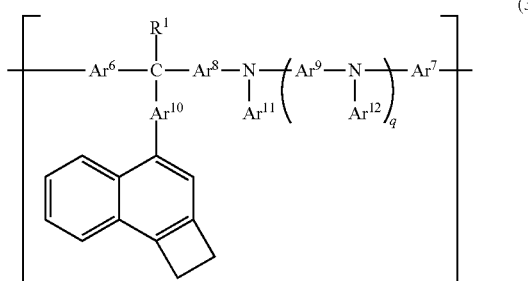

(3)

wherein q represents an integer of 0 to 3,
$R^1$ represents an alkyl group of 1 to 24 carbon atoms that may have a substituent, an aromatic hydrocarbon group that may have a substituent, or an aromatic heterocyclic group that may have a substituent,
$Ar^6$ and $Ar^7$ each independently represents a direct bond, an aromatic hydrocarbon group that may have a substituent, or an aromatic heterocyclic group that may have a substituent,
$Ar^8$ to $Ar^{12}$ each independently represents an aromatic hydrocarbon group that may have a substituent, or an aromatic heterocyclic group that may have a substituent, and the $Ar^6$ and $Ar^7$ are not direct bonds at the same time.

[4] The polymer according to the [1] above, which comprises a repeating unit represented by the following formula (4):

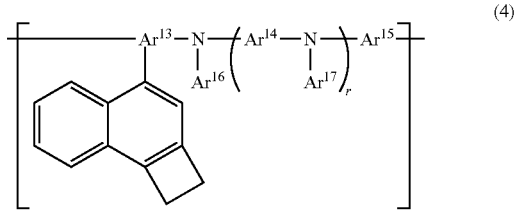

(4)

wherein r represents an integer of 0 to 3,
$Ar^{13}$, $Ar^{14}$, $Ar^{16}$, and $Ar^{17}$ each independently represent an aromatic hydrocarbon group that may have a substituent, or an aromatic heterocyclic group that may have a substituent, and
$Ar^{15}$ represents a direct bond, an aromatic hydrocarbon group that may have a substituent, or an aromatic heterocyclic group that may have a substituent.

[5] The polymer according to any one of the [1] to [4] above, which has a weight-average molecular weight (Mw) of 20,000 or more, and a degree of dispersion (Mw/Mn) of 2.5 or less.

[6] A composition for organic electroluminescent element, which comprises the polymer of any one of the [1] to [5] above.

[7] An organic electroluminescent element comprising a substrate, an anode and a cathode provided on the substrate, and an organic layer provided between the anode and the cathode, wherein the organic layer contains a layer formed by a wet film formation method using the composition for organic electroluminescent element of the [6] above.

[8] The organic electroluminescent element according to the [7] above, wherein the layer formed by a wet film formation method is at least one of a hole injection layer and a hole transport layer.

[9] The organic electroluminescent element according to the [7] or [8] above, which comprises a hole injection layer, a hole transport layer and a light-emitting layer between the anode and the cathode, wherein the hole injection layer, the hole transport layer, and the light-emitting layer are all formed by a wet film formation method.

[10] An organic EL display device comprising the organic electroluminescent element of any one of the [7] to [9] above.

[11] An organic EL lighting device comprising the organic electroluminescent element of any one of the [7] to [9] above.

[12] A compound represented by the following formula (5):

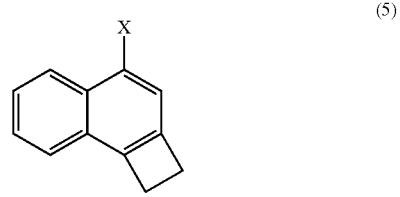

(5)

wherein X represents a halogen atom.

Advantageous Effects of Invention

A layer obtained by using wet film formation with a composition for organic electroluminescent elements containing a polymer of the present invention is a flat layer that does not have defects such as cracking. An organic electroluminescent element of the present invention has high luminance, and a long drive lifetime.

BRIEF DESCRIPTION OF DRAWINGS

The FIGURE is a schematic view of a cross section representing an exemplary structure of an organic electroluminescent element of the present invention.

DESCRIPTION OF EMBODIMENTS

The following will describe an embodiment of the present invention in detail. The descriptions of the constituting elements below merely represent an example (typical example) of the embodiment of the present invention, and the substance of the following descriptions does not specify the present invention, so long as the descriptions below fall within the gist of the present invention.

As used herein, percentages and parts represented by "mass" have the same definitions as percentages and parts represented by "weight".

<Polymer>

A polymer of the present invention has a crosslinkable group represented by the following formula (1).

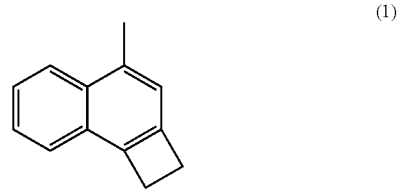

(1)

(In formula (1), the 1,2-dihydrocyclobuta[a]naphthalene ring may have a substituent.)

The substituent on the 1,2-dihydrocyclobuta[a]naphthalene ring in formula (1) when it is substituted is preferably one that is unlikely to interfere with the crosslinking reaction. Specific examples of such substituents include an alkyl group of 1 to 12 carbon atoms, and an alkoxy group of 1 to 12 carbon atoms.

The crosslinkable group represented by formula (1) opens its ring under heat, as shown in the reaction formula (6) below. The activation energy of the ring-opening reaction represented by the following reaction formula (6) is smaller than the activation energy of the ring-opening reaction of the conventional crosslinkable group benzocyclobutene.

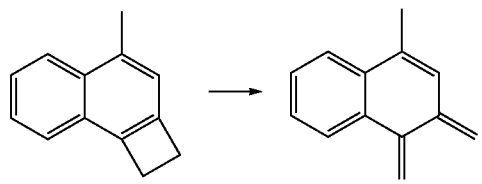

(6)

The opening of the ring is followed by the addition reaction, as shown in the following reaction formula (7).

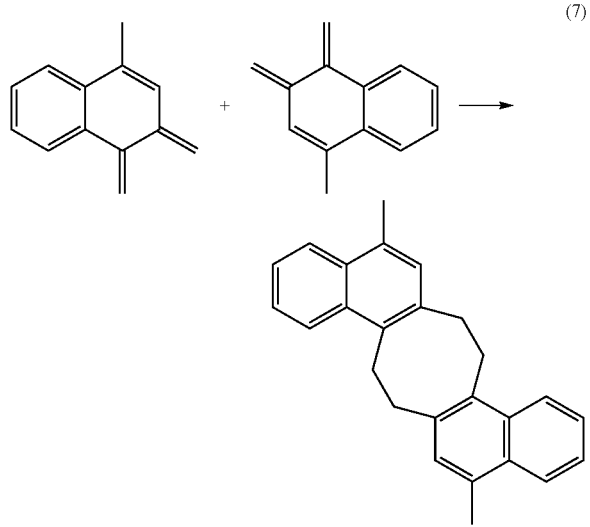

(7)

In a series of crosslinking reactions, a ring-opening reaction typically requires a higher activation energy than an addition reaction. It is accordingly possible to insolubilize a polymer at low temperatures in a short time period when the polymer contains the 1,2-dihydrocyclobuta[a]naphthalene of formula (1) as a crosslinkable group requiring a small activation energy for the ring-opening reaction.

Specifically, the low-temperature insolubilization rate of the polymer having a crosslinkable group represented by the formula (1) is dependent on the crosslinkable group represented by the formula (1), and the foregoing mechanism makes the polymer of the present invention insolubilizable at low temperatures in a short time period.

Examples of partial structures that are suited for charge transport include triarylamine structures; aromatic ring structures with three or more rings, such as a fluorene ring, an anthracene ring, a pyrene ring, a carbazole ring, a dibenzofuran ring, a dibenzothiophene ring, a phenoxazine ring, and a phenanthroline ring; aromatic heterocyclic ring structures such as a pyridine ring, a pyrazine ring, a triazine ring, a quinoline ring, a thiophene ring, a silole ring, an imidazole ring, a pyrazole ring, an oxadiazole ring, and a benzothiadiazole ring; and metal complex structures. Triarylamine structures are preferred for their excellent hole transporting ability.

From the standpoint of improving charge transporting ability, the polymer of the present invention preferably contains a repeating unit represented by the following formula (2).

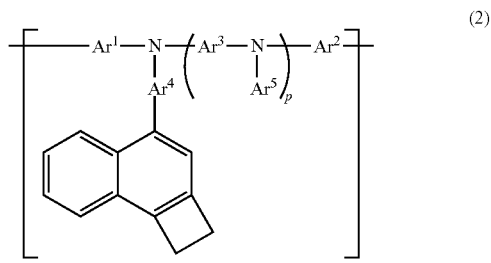

(2)

(In the formula (2), p represents an integer of 0 to 3, $Ar^1$ and $Ar^2$ each independently represent a direct bond, an aromatic hydrocarbon group that may have a substituent, or an aromatic heterocyclic group that may have a substituent, $Ar^3$ to $Ar^5$ each independently represent an aromatic hydrocarbon group that may have a substituent, or an aromatic heterocyclic group that may have a substituent, wherein $Ar^1$ and $Ar^2$ are not direct bonds at the same time.)

The crosslinkable group in formula (2) exists via at least one single bond from the triarylamine structure, and charge transporting ability further improves because the crosslinkable group is unlikely to become an obstacle for charge transport.

From the standpoints of improving charge transporting ability and achieving insolubilization under milder conditions, the polymer of the present invention preferably contains a repeating unit represented by the following formula (3).

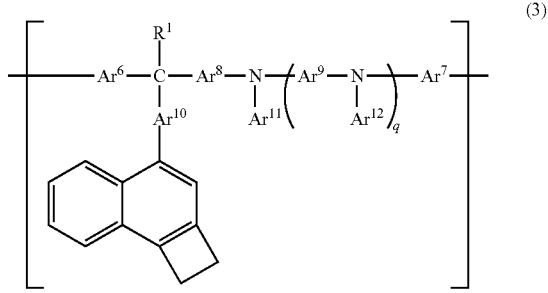

(3)

(In formula (3), q represents an integer of 0 to 3, $R^1$ represents an alkyl group of 1 to 24 carbon atoms that may have a substituent, an aromatic hydrocarbon group that may have a substituent, or an aromatic heterocyclic group that may have a substituent, Ar$^6$ and Ar$^7$ each independently represent a direct bond, an aromatic hydrocarbon group that may have a substituent, or an aromatic heterocyclic group that may have a substituent.

Ar$^8$ to Ar$^{12}$ each independently represent an aromatic hydrocarbon group that may have a substituent, or an aromatic heterocyclic group that may have a substituent, wherein Ar$^6$ and Ar$^7$ are not direct bonds at the same time.)

The carbon atom at the center of the sp3 hybrid orbitals in formula (3) does not take part in the π conjugate system, and as such the side-chain crosslinkable group attached to the center carbon atom of the sp3 hybrid orbitals is unlikely to become an obstacle for charge transport. This further improves charge transporting ability.

The center atom of sp3 hybrid orbitals more easily allows for bond rotation than the center atom of sp2 hybrid orbitals, and the crosslinkable group in the polymer can more efficiently undergo reaction. The polymer can thus become poorly soluble for organic solvent even when the number of crosslinkable groups is small, or when the crosslinking reaction is performed under mild conditions.

From the standpoint of improving charge transporting ability, the polymer of the present invention preferably contains a repeating unit represented by the following formula (4).

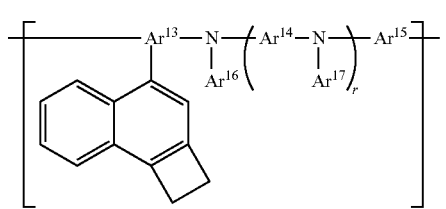

(4)

(In formula (4), r represents an integer of 0 to 3,

Ar$^{13}$, Ar$^{14}$, Ar$^{16}$, and Ar$^{17}$ each independently represent an aromatic hydrocarbon group that may have a substituent, or an aromatic heterocyclic group that may have a substituent, and Ar$^{15}$ represents a direct bond, an aromatic hydrocarbon group that may have a substituent, or an aromatic heterocyclic group that may have a substituent.)

The crosslinkable group in formula (4) exists via at least one single bond from the arylene group on the main chain, and charge transporting ability further improves because the crosslinkable group is unlikely to become an obstacle for charge transport.

[Ar$^1$ to Ar$^{17}$]

In formulae (2) to (4), Ar$^1$, Ar$^2$, Ar$^6$, Ar$^7$, and Ar$^{15}$ each represent a direct bond, a divalent aromatic hydrocarbon group that may have a substituent, or a divalent aromatic heterocyclic group that may have a substituent. The aromatic hydrocarbon group and the aromatic heterocyclic group may represent a plurality of aromatic hydrocarbon groups or aromatic heterocyclic groups that are bonded to each other.

Ar$^3$, Ar$^4$, Ar$^8$, Ar$^9$, Ar$^{10}$, and Ar$^{14}$ each represent a divalent aromatic hydrocarbon group that may have a substituent, or a divalent aromatic heterocyclic group that may have a substituent. The aromatic hydrocarbon group and the aromatic heterocyclic group may represent a plurality of aromatic hydrocarbon groups or aromatic heterocyclic groups that are bonded to each other.

Ar$^{13}$ represents a trivalent aromatic hydrocarbon group that may have a substituent, or a trivalent aromatic heterocyclic group that may have a substituent. The aromatic hydrocarbon group and the aromatic heterocyclic group may represent a plurality of aromatic hydrocarbon groups or aromatic heterocyclic groups that are bonded to each other.

Ar$^5$, Ar$^{11}$, Ar$^{12}$, Ar$^{16}$, and Ar$^{17}$ each represent a monovalent aromatic hydrocarbon group that may have a substituent, or a monovalent aromatic heterocyclic group that may have a substituent. The aromatic hydrocarbon group and the aromatic heterocyclic group may represent a plurality of aromatic hydrocarbon groups or aromatic heterocyclic groups that are bonded to each other.

The aromatic hydrocarbon ring group is preferably of 6 to 30 carbon atoms. Examples of such aromatic hydrocarbon ring groups include monovalent or divalent groups of a six-membered monocyclic ring or fused rings of 2 to 5 six-membered rings, such as a benzene ring, a naphthalene ring, an anthracene ring, a phenanthrene ring, a perylene ring, a tetracene ring, a pyrene ring, a benzopyrene ring, a chrysene ring, a triphenylene ring, an acenaphthene ring, a fluoranthene ring, and a fluorene ring.

The aromatic heterocyclic group is preferably of 3 to 30 carbon atoms. Examples of such aromatic heterocyclic groups include monovalent or divalent groups of a five- or six-membered monocyclic ring or fused rings of 2 to 4 five- or six-membered rings, such as a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzoisooxazole ring, a benzoisothiazole ring, a benzoimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzoimidazole ring, a perimidine ring, a quinazoline ring, a quinazolinone ring, and an azulene ring.

Aromatic hydrocarbon ring groups, particularly divalent groups of a benzene ring and a fluorene ring are preferred for their excellent charge transporting ability and durability. Specifically, a phenylene group, and a fluorenylene group are more preferred, and a 1,3-phenylene group, a 1,4-phenylene group, and a 2,7-fluorenyl group are further preferred.

When the aromatic hydrocarbon group and the aromatic heterocyclic group represent a plurality of aromatic hydrocarbon groups or aromatic heterocyclic groups that are bonded to each other, it is preferable that 2 to 6 aromatic hydrocarbon groups or aromatic heterocyclic groups be joined to each other from the standpoint of providing excellent charge transporting ability and durability. The aromatic hydrocarbon groups and the aromatic heterocyclic groups that are joined to each other may be the same or different.

When the aromatic hydrocarbon group and the aromatic heterocyclic group represent a plurality of aromatic hydrocarbon groups or aromatic heterocyclic groups that are bonded to each other, these may be attached via a linking group. In this case, the linking group is preferably a group selected from the group consisting of —CR$^2$R$^3$—, —O—, —CO—, —NR$^4$—, and —S—, or a group formed by joining 2 to 10 of these groups. When two or more linking groups are joined to each other, the linking groups may be the same or different. Here, R$^2$ to R$^4$ each independently represent a hydrogen atom, an alkyl group of 1 to 24 carbon atoms that may have a substituent, an aromatic hydrocarbon group that may have a substituent, or an aromatic heterocyclic group that may have a substituent. Particularly preferred as the linking group are —CR$^2$R$^3$—, and 2 to 6 —CR$^2$R$^3$— groups that are joined to each other, of which —CR$^2$R$^3$— is more preferred.

The substituents of the aromatic hydrocarbon ring group and the aromatic heterocyclic group when these are substituted are not particularly limited, as long as it is not detrimental to the polymer characteristics. Examples include groups selected from the following substituent group Z, preferably an alkyl group, an alkoxy group, an aromatic hydrocarbon ring group, and an aromatic heterocyclic group, more preferably an alkyl group.

[Substituent Group Z]

Linear, branched, or cyclic alkyl groups of typically 1 or more carbon atoms, and typically 24 or less, preferably 12 or less carbon atoms, for example, such as a methyl group, an ethyl group, an n-propyl group, an i-propyl group, an n-butyl group, an i-butyl group, a sec-butyl group, a tert-butyl group, an n-hexyl group, a cyclohexyl group, and a dodecyl group;

alkenyl groups of typically 2 or more carbon atoms, and typically 24 or less, preferably 12 or less carbon atoms, for example, such as a vinyl group;

alkynyl groups of typically 2 or more carbon atoms, and typically 24 or less, preferably 12 or less carbon atoms, for example, such as an ethynyl group;

alkoxy groups of typically 1 or more carbon atoms, and typically 24 or less, preferably 12 or less carbon atoms, for example, such as a methoxy group, and an ethoxy group;

aryloxy groups of typically 4 or more, preferably 5 or more carbon atoms, and typically 36 or less, preferably 24 carbon atoms, for example, such as a phenoxy group, a naphthoxy group, and a pyridyloxy group;

alkoxycarbonyl groups of typically 2 or more carbon atoms, and typically 24 or less, preferably 12 or less carbon atoms, for example, such as a methoxycarbonyl group, and an ethoxycarbonyl group;

dialkylamino groups of typically 2 or more carbon atoms, and typically 24 or less, preferably 12 or less carbon atoms, for example, such as a dimethylamino group, and a diethylamino group;

diarylamino groups of typically 10 or more, preferably 12 or more carbon atoms, and typically 36 or less, preferably 24 or less carbon atoms, for example, such as a diphenylamino group, a ditolylamino group, and an N-carbazolyl group;

arylalkylamino groups of typically 7 or more carbon atoms, and typically 36 or less, preferably 24 or less carbon atoms, for example, such as a phenylmethylamino group;

acyl groups of typically 2 or more carbon atoms, and typically 24 or less, preferably 12 or less carbon atoms, for example, such as an acetyl group, and a benzoyl group;

halogen atoms, for example, such as a fluorine atom, and a chlorine atom;

haloalkyl groups of typically 1 or more carbon atoms, and typically 12 or less, preferably 6 or less carbon atoms, for example, such as a trifluoromethyl group;

alkylthio groups of typically 1 or more carbon atoms, and typically 24 or less, preferably 12 or less carbon atoms, for example, such as a methylthio group, and an ethylthio group;

arylthio groups of typically 4 or more, preferably 5 or more carbon atoms, and typically 36 or less, preferably 24 or less carbon atoms, for example, such as a phenylthio group, a naphthylthio group, and a pyridylthio group;

silyl groups of typically 2 or more, preferably 3 or more carbon atoms, and typically 36 or less, preferably 24 or less carbon atoms, for example, such as a trimethylsilyl group, and a triphenylsilyl group;

siloxy groups of typically 2 or more, preferably 3 or more carbon atoms, and typically 36 or less, preferably 24 or less carbon atoms, for example, such as a trimethylsiloxy group, and a triphenylsiloxy group;

cyano groups;

aromatic hydrocarbon ring groups of typically 6 or more carbon atoms, and typically 36 or less, preferably 24 or less carbon atoms, for example, such as a phenyl group, and a naphthyl group;

aromatic heterocyclic groups of typically 3 or more, preferably 4 or more carbon atoms, and typically 36 or less, preferably 24 or less carbon atoms, for example, such as a thienyl group, and a pyridyl group.

Of these substituents, preferred for solubility are alkyl groups of 1 to 12 carbon atoms, and alkoxy groups of 1 to 12 carbon atoms.

The substituents may have a further substituent. Examples of such further substituents include ones selected from the group exemplified in the [Substituent Group Z] section above.

[R$^1$]

In formula (3), R$^1$ represents a hydrogen atom, an alkyl group of 1 to 24 carbon atoms that may have a substituent, an aromatic hydrocarbon group that may have a substituent, or an aromatic heterocyclic group that may have a substituent. The alkyl group is a linear, branched, or cyclic alkyl group of typically 1 or more carbon atoms, and typically 24 or less, preferably 12 or less carbon atoms. Specific examples include a methyl group, an ethyl group, an n-propyl group, an i-propyl group, an n-butyl group, an i-butyl group, a sec-butyl group, a tert-butyl group, an n-hexyl group, a cyclohexyl group, and a dodecyl group. When R$^1$ is an aromatic hydrocarbon group that may have a substituent, or an aromatic heterocyclic group that may have a substituent, specific examples and preferred examples of R$^1$ are the same as for Ar$^5$, Ar$^{11}$, Ar$^{12}$, Ar$^{16}$, and Ar$^{17}$.

In formulae (2) to (4), p, q, and r are each an integer of 0 to 3. p, q, and r are each preferably 2 or less.

[Molecular Weight of Polymer]

The polymer of the present invention has a weight-average molecular weight (Mw) of typically 3,000,000 or less, preferably 1,000,000 or less, more preferably 500,000 or less, further preferably 200,000 or less, and typically 2,500 or more, preferably 5,000 or more, more preferably 10,000 or more, further preferably 20,000 or more, particularly preferably 30,000 or more.

When the weight-average molecular weight of the polymer exceeds the foregoing upper limits, solubility for solvent decreases, and ease of deposition may suffer. On the other hand, when the weight-average molecular weight of the polymer falls below the foregoing lower limits, the glass transition point, the melting point, and the vaporization temperature of the polymer decrease, and the heat resistance may suffer.

The number average molecular weight (Mn) of the polymer of the present invention is typically 2,500,000 or less, preferably 750,000 or less, more preferably 400,000 or less, and typically 2,000 or more, preferably 4,000 or more, more preferably 8,000 or more, further preferably 20,000 or more.

The polymer of the present invention has a degree of dispersion (Mw/Mn) of preferably 3.5 or less, further preferably 2.5 or less, particularly preferably 2.0 or less. The lower limit of the degree of dispersion is 1. Solubility for solvent, and charge transporting ability become desirable when the degree of dispersion of the polymer is at or below the upper limit.

It is preferable in the present invention that the polymer of the present invention have a weight-average molecular weight or 20,000 or more, and a degree of dispersion of 2.5 or less. A polymer with a weight-average molecular weight and a degree of dispersion falling in these ranges is preferable because such a polymer contains small amounts of low-molecular-weight components, and is sufficiently insolubilizable.

linkable groups for a polymer molecular weight of 1,000 can be calculated from the molar ratio of the material monomer used in synthesis, excluding the terminal groups of the polymer, and from the structural formula. For example, in the case of the polymer 1 synthesized in Examples below, the average molecular weight of the repeating unit in the polymer 1 excluding the terminal groups is 840.71, and the number of crosslinkable groups per repeating unit is, on average, 0.111. It follows from simple proportionality that the number of crosslinkable groups for a molecular weight of 1,000 is 0.13.

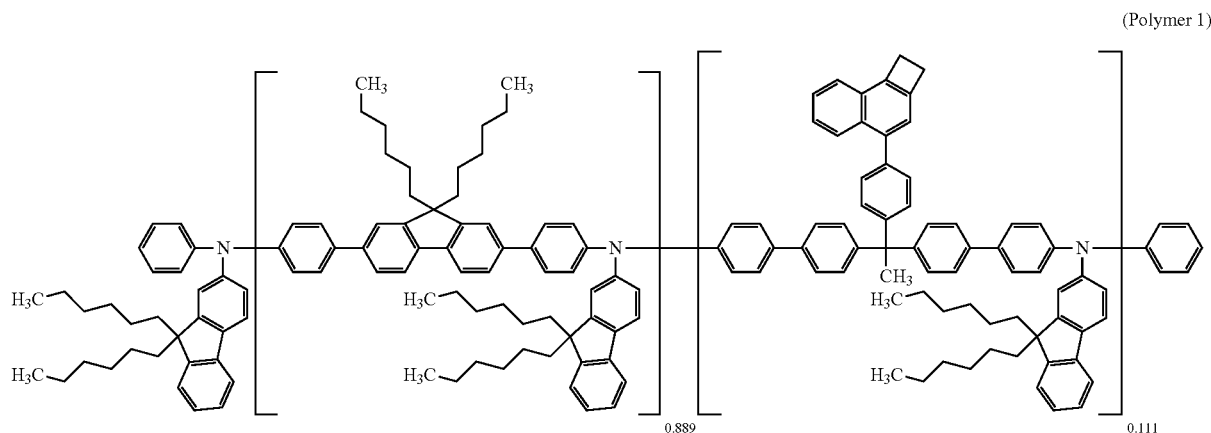

(Polymer 1)

Typically, the weight-average molecular weight, and the degree of dispersion of the polymer are determined by SEC (size-exclusion chromatography) measurement. An SEC measurement yields shorter elution times for components with higher molecular weights, and longer elution times for components with lower molecular weights. The weight-average molecular weight, and the degree of dispersion are thus calculated by converting the sample elution time into a molecular weight, using a calibration curve calculated from the elution time of a polystyrene (standard sample) of a known molecular weight.

[Number of Crosslinkable Groups]

Preferably, the polymer of the present invention contains larger numbers of crosslinkable groups from the standpoint of sufficiently achieving insolubilization through crosslinking, and enabling easy formation of other layers using a wet film formation method. It is, however, preferable that the crosslinkable groups are contained in smaller numbers from the standpoints of preventing cracking in the formed layers, reducing the number of unreacted crosslinkable groups, and increasing the lifetime of the organic electroluminescent element.

In the polymer of the present invention, the number of crosslinkable groups per polymer chain, on average, is typically 1 or more, preferably 2 or more, and typically 200 or less, preferably 100 or less.

The number of crosslinkable groups in the polymer of the present invention may be expressed as a number for a polymer molecular weight of 1,000. The number of cross- The number of crosslinkable groups in the polymer of the present invention is typically 3.0 or less, preferably 2.0 or less, further preferably 1.0 or less, and typically 0.01 or more, preferably 0.05 or more in terms of a number for a polymer molecular weight of 1,000.

When the number of crosslinkable groups falls in these ranges, defects such as cracking are unlikely to occur, and it becomes easier to obtain a flat film. Further, because of the moderate crosslink density, only a few crosslinkable groups remain unreacted in the layer after the crosslinking reaction, and the impact of such unreacted crosslinkable groups on the lifetime of the product element becomes smaller.

Further, because the solubility for organic solvent is sufficiently poor after the crosslinking reaction, it becomes easier to form a multilayer laminate structure using a wet film formation method.

SPECIFIC EXAMPLES

Specific examples of the polymer of the present invention are given below.

The polymers may have any form, including random copolymers, alternate copolymers, block copolymers, and graft copolymers, and the order of monomer sequence is not limited.

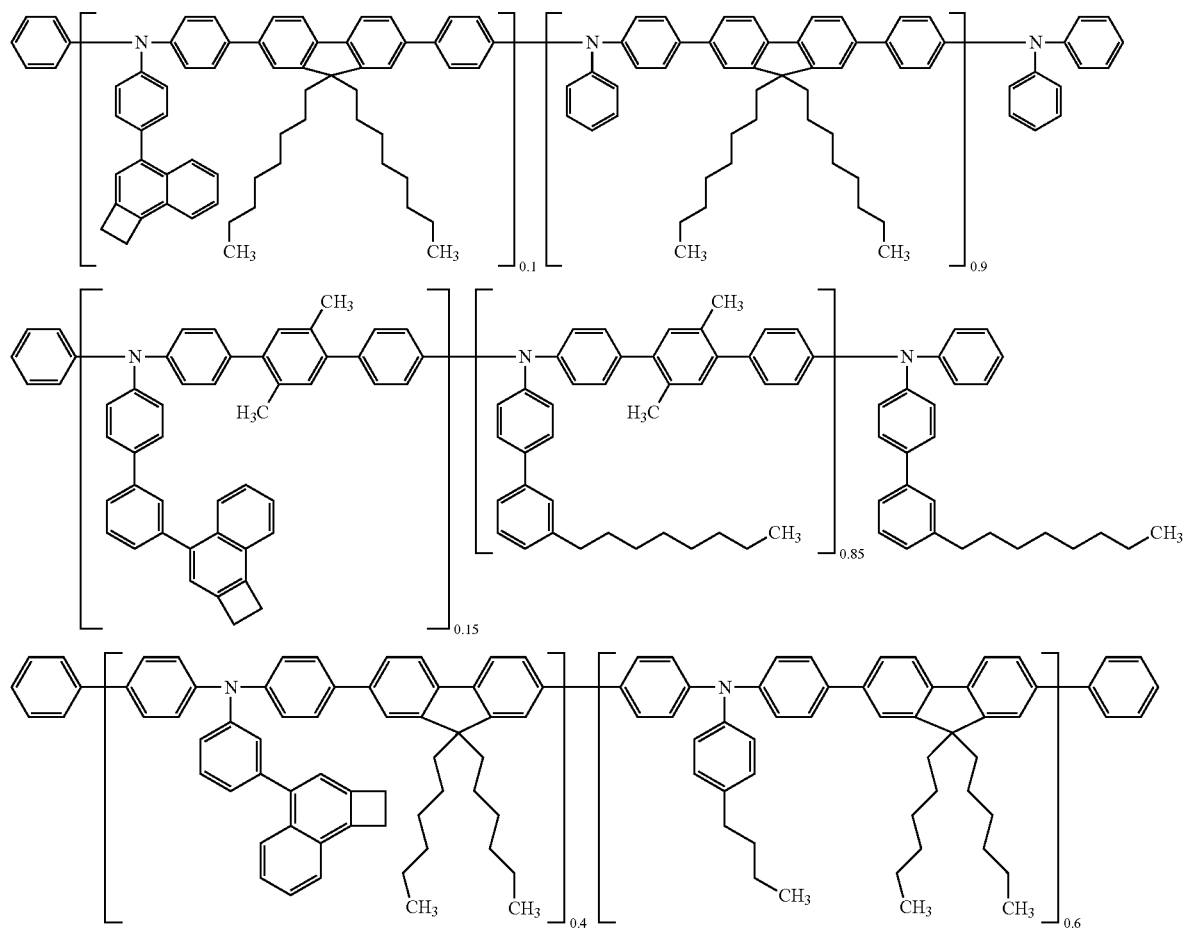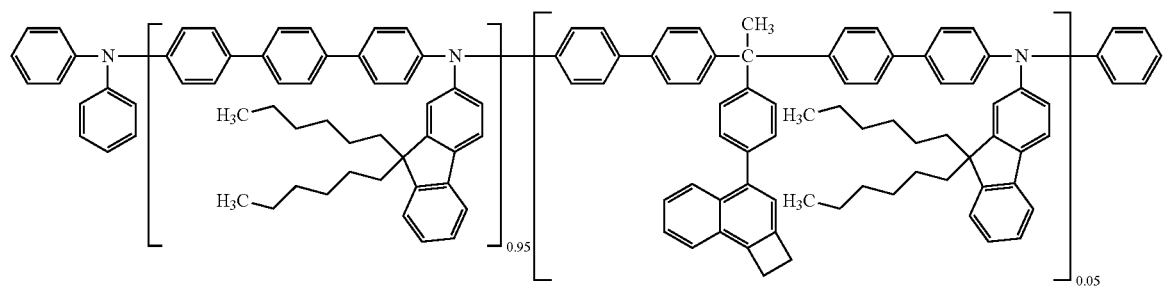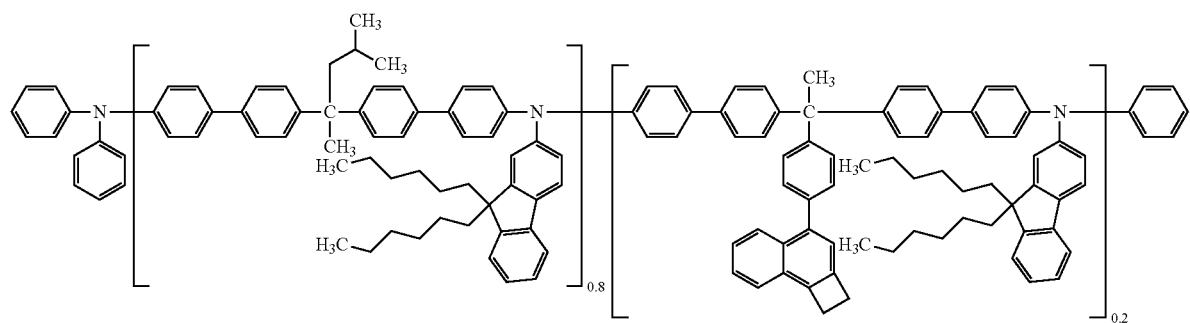

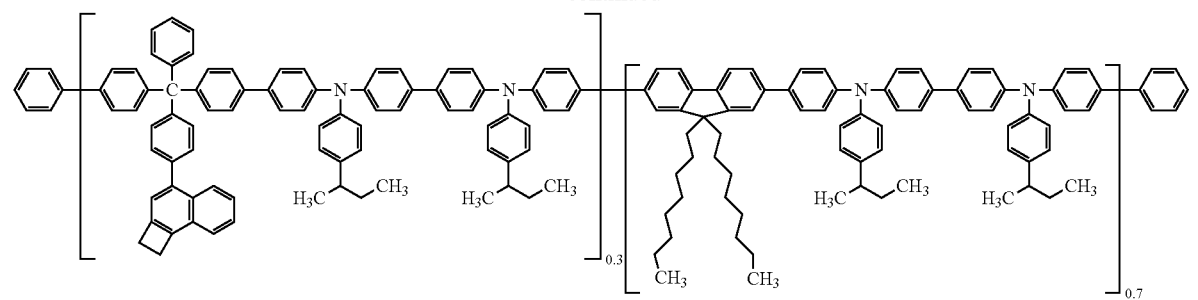
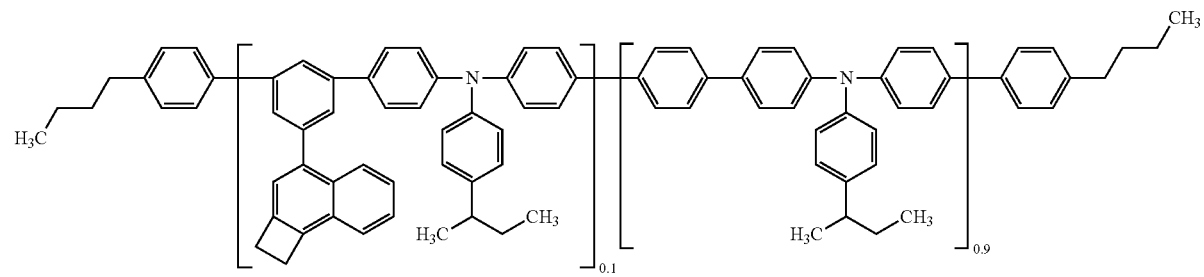
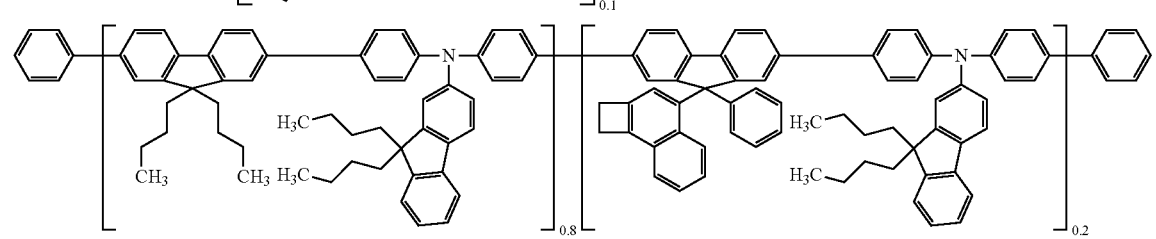
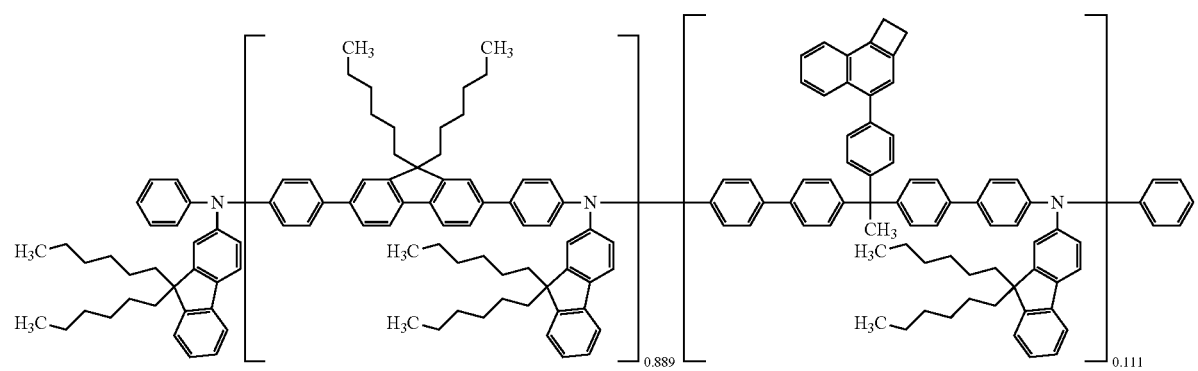
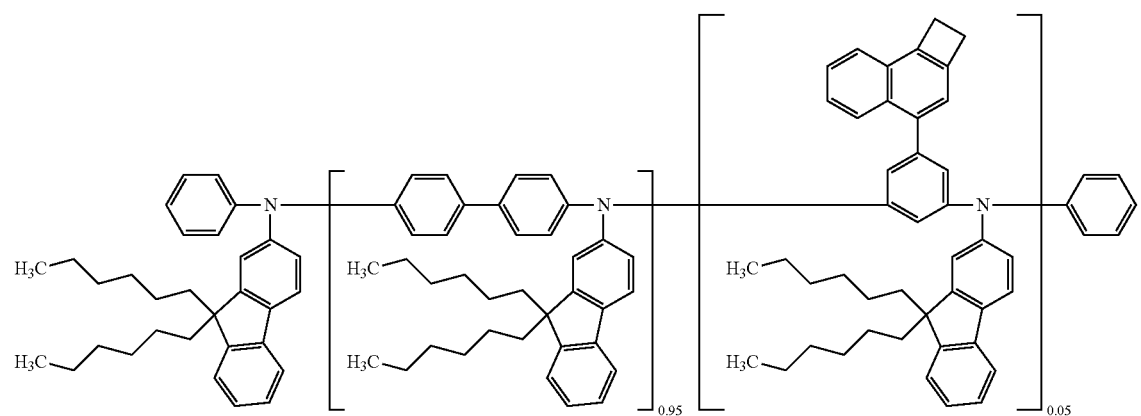

-continued

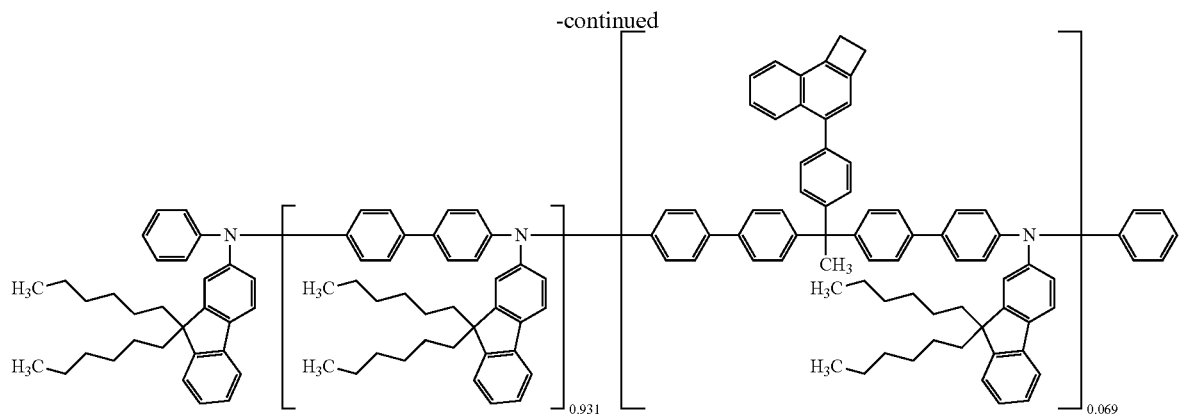

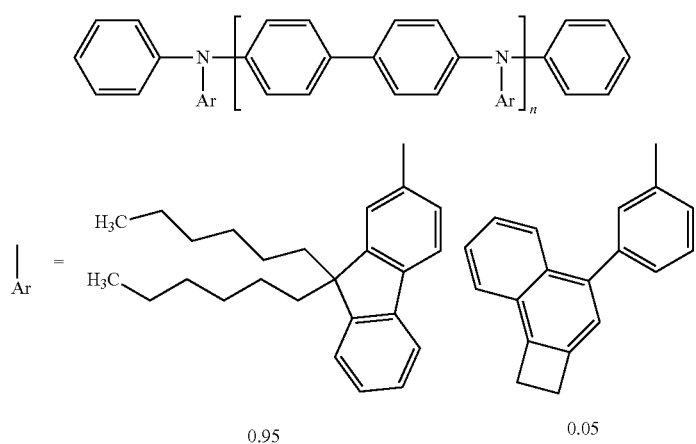

The polymer of the present invention is preferably used for an organic electroluminescent element having an insulating film made of resin. This is because insulating resin films have a relatively low heat resistance, and degradation and a gas release from the insulating resin film can be reduced when the production of the organic electroluminescent element involves a low temperature. As used herein, "insulating resin film" refers to a leveling film for covering anodes, auxiliary electrodes, or some other irregularities on a substrate, or a film for compartmentalizing the electrodes, and encompasses dividing walls that compartmentalize pixels and emission regions. By "some other irregularities", it means, for example, a particle-containing layer for scattering light, or TFTs provided in a display device. The insulating film resin is preferably a polyimide resin, a polyolefinic resin, or an acrylic resin. The polymer of the present invention is more preferably used for an organic electroluminescent element for organic EL display devices in which a insulating resin film is used.

<Synthesis Method>

A monomer having a crosslinkable group represented by formula (1) in the polymer of the present invention can be synthesized via a halide represented by formula (5).

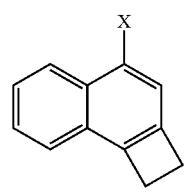

(5)

(In formula (5), X represents a halogen atom.)

Examples of the halogen atom in formula (5) include I, Br, Cl, and F. I, Br, and Cl are preferred for ease of the reaction below.

The halide represented by formula (5) can be efficiently obtained from 1,2-dihydrocyclobuta[a]naphthalene, which becomes selectively halogenated at the 4-position upon being acted upon by the N-halide of carboxylic acid imides such as N-bromosuccinimide, and N-bromophthalimide, as represented by the following reaction formula (8).

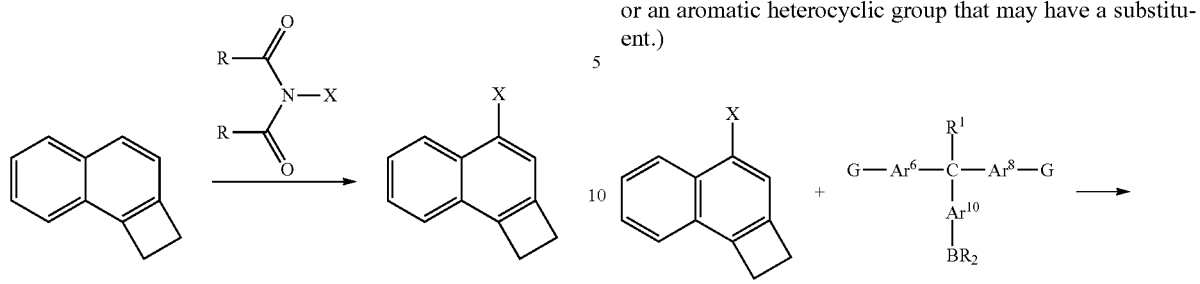

(In the reaction formula, X represents a halogen atom.)

Bromine has been used to obtain halides of the conventional crosslinkable group benzocyclobutene, as represented by the reaction formula (9) below (European Patent No. 346959, J. Am. Chem. Soc. 2011, No. 133, Vol. 49, p. 19864). However, bromine acting on 1,2-dihydrocyclobuta[a]naphthalene brominates positions other than the 4-position, and cannot efficiently yield the target product.

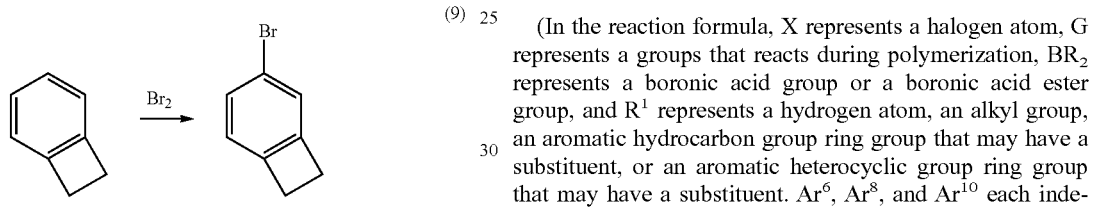

Known coupling techniques can be used as a method of inducing the halide of formula (5) to a monomer. For example, the Suzuki reaction is used for synthesis, as follows.

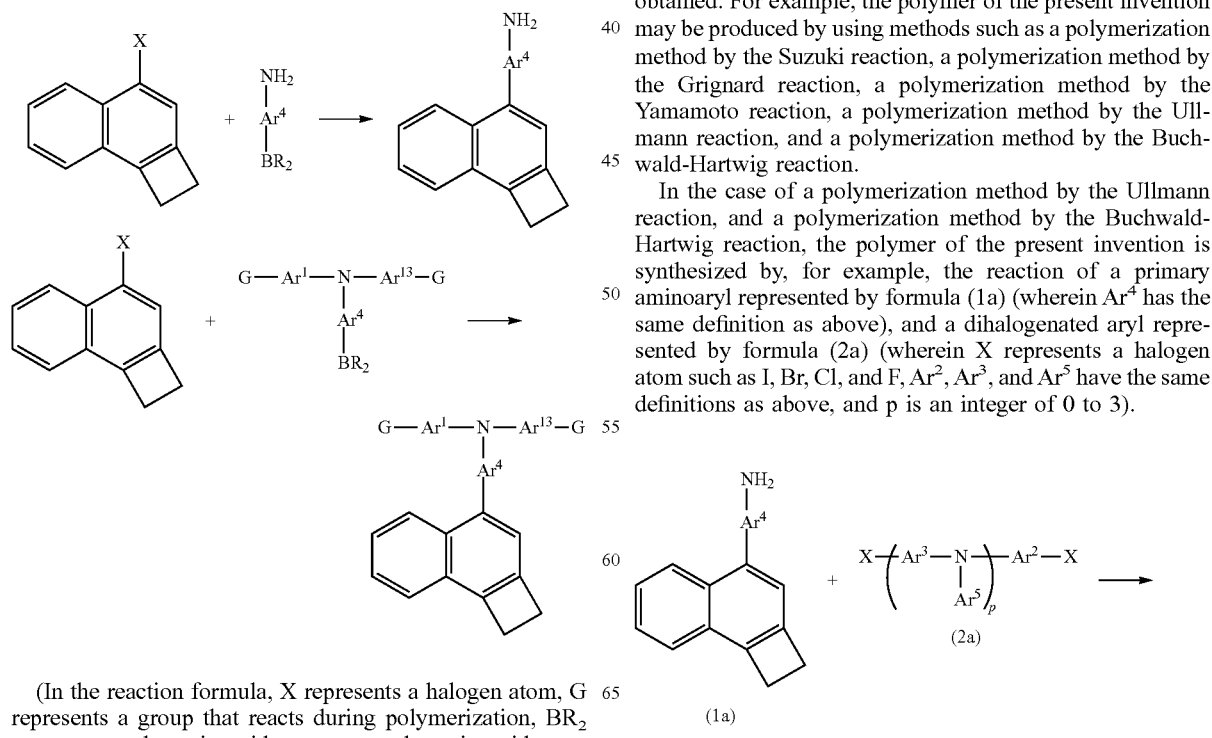

(In the reaction formula, X represents a halogen atom, G represents a group that reacts during polymerization, $BR_2$ represents a boronic acid group or a boronic acid ester group, and $Ar^1$, $Ar^4$, and $Ar^{13}$ each independently represent an aromatic hydrocarbon group that may have a substituent, or an aromatic heterocyclic group that may have a substituent.)

(In the reaction formula, X represents a halogen atom, G represents a groups that reacts during polymerization, $BR_2$ represents a boronic acid group or a boronic acid ester group, and $R^1$ represents a hydrogen atom, an alkyl group, an aromatic hydrocarbon group ring group that may have a substituent, or an aromatic heterocyclic group ring group that may have a substituent. $Ar^6$, $Ar^8$, and $Ar^{10}$ each independently represent an aromatic hydrocarbon group that may have a substituent, or an aromatic heterocyclic group that may have a substituent.)

The method of production of the polymer of the present invention is not particularly limited, and any method may be used, as long as the polymer of the present invention is obtained. For example, the polymer of the present invention may be produced by using methods such as a polymerization method by the Suzuki reaction, a polymerization method by the Grignard reaction, a polymerization method by the Yamamoto reaction, a polymerization method by the Ullmann reaction, and a polymerization method by the Buchwald-Hartwig reaction.

In the case of a polymerization method by the Ullmann reaction, and a polymerization method by the Buchwald-Hartwig reaction, the polymer of the present invention is synthesized by, for example, the reaction of a primary aminoaryl represented by formula (1a) (wherein $Ar^4$ has the same definition as above), and a dihalogenated aryl represented by formula (2a) (wherein X represents a halogen atom such as I, Br, Cl, and F, $Ar^2$, $Ar^3$, and $Ar^5$ have the same definitions as above, and p is an integer of 0 to 3).

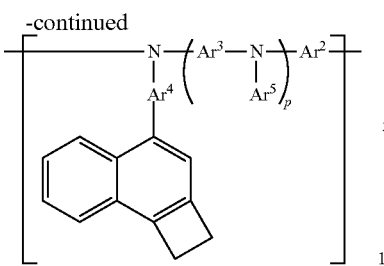

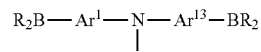

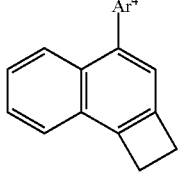

(1b)

The polymer of the present invention is also synthesized by the reaction of a dihalogenated aryl represented by formula (3a) (wherein X represents a halogen atom such as I, Br, Cl, and F, and $R^1$, $Ar^6$, $Ar^8$, and $Ar^{10}$ have the same definitions as above), and a primary or secondary aminoaryl represented by formula (4a) (wherein $Ar^9$, $Ar^{11}$, and $Ar^{12}$ have the same definitions as above, and q is an integer of 0 to 3.).

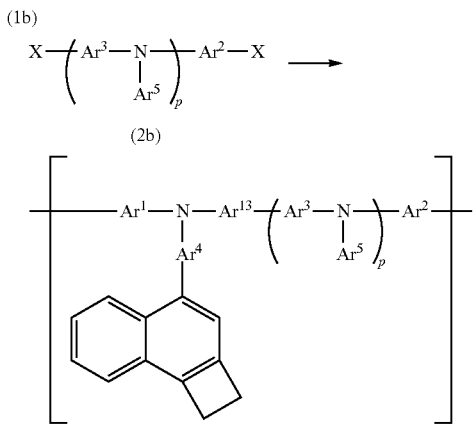

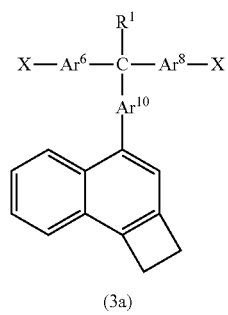

(3a)

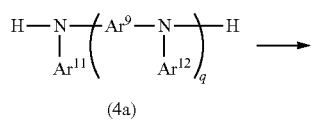

(4a)

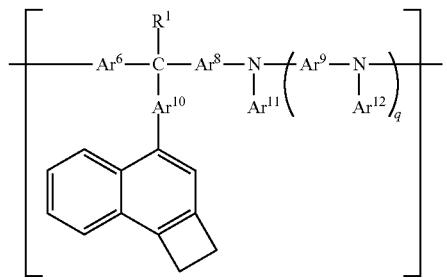

The polymer of the present invention is also synthesized by, for example, the reaction of a boron derivative represented by formula (3b) (wherein $BR_2$ represents a boronic acid group or a boronic acid ester group, and $R^1$, $Ar^6$, $Ar^8$, and $Ar^{10}$ have the same definitions as above), and a dihalogenated aryl represented by formula (4b) (wherein X represents a halogen atom such as I, Br, Cl, and F, $Ar^9$, $Ar^{10}$, and $Ar^{12}$ have the same definitions as above, and p is an integer of 0 to 3.).

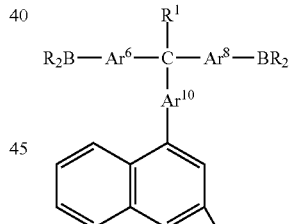

(3b)

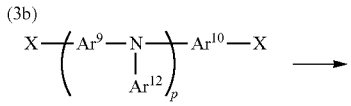

(4b)

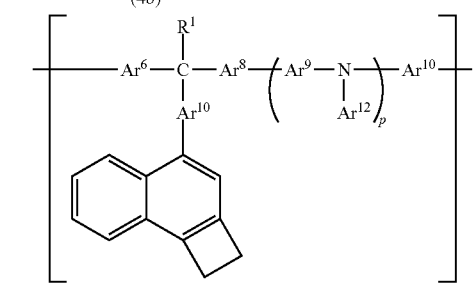

In the polymerization methods above, the reaction that forms the N-aryl bond is typically performed in the presence of a base, for example, such as potassium carbonate, tert-butoxysodium, and triethylamine. The reaction also may be performed in the presence of a transition metal catalyst, for example, such as copper, and a palladium complex.

In the case of a polymerization method by the Suzuki reaction, the polymer of the present invention is synthesized by, for example, the reaction of a boron derivative represented by formula (1b) (wherein $BR_2$ represents a boronic acid group or a boronic acid ester group, and $Ar^1$, $Ar^4$, and $Ar^{13}$ have the same definitions as above), and a dihalogenated aryl represented by formula (2b) (wherein X represents a halogen atom such as I, Br, Cl, and F, $Ar^2$, $Ar^3$, and $Ar^5$ have the same definitions as above, and p is an integer of 0 to 3.).

In the polymerization methods above, the reaction steps involving the boron derivative and the dihalide are typically performed in the presence of a base, for example, such as potassium carbonate, tert-butoxysodium, and triethylamine. The reaction also may be performed in the presence of a transition metal catalyst, for example, such as copper, and a palladium complex, as required. The reaction steps involving the boron derivative may be performed in the presence of a base, for example, such as potassium carbonate, potassium phosphate, tert-butoxysodium, and triethylamine, and in the presence of a transition metal catalyst such as a palladium complex.

Aside from the foregoing polymerization methods, the charge-transporting polymer of the present invention also may be produced by using the polymerization methods described in JP-A-2001-223084, JP-A-2003-213002, and JP-A-2004-2740, or through radical polymerization of a compound having an unsaturated double bond, or sequential polymerization by a reaction that forms an ester bond or an amide bond.

Other known coupling reactions are also usable. Specific examples of known coupling techniques include ring coupling reactions, such as the coupling reaction between a halogenated aryl and an aryl borate described or cited in various publications, including *Palladium in Heterocyclic Chemistry: A Guide for the Synthetic Chemist* (2nd Ed., 2002, Jie Jack Li and Gordon W. Gribble, Pergamon), *Transition metals Open the Door for Organic Synthesis, A Diverse Form of Reaction and the Latest Findings* (*Sen-i Kinzoku ga Hiraku Yuuki Gousei, Sono Tasai na Hannou Keishiki to Saishin no Seika;* 1997, Jiro Tsuji, Kagakudojin), and *Vollhardt-Schore Organic Chemistry*, 2nd Volume (*Vollhardt-Schore, Gendai Yuuki Kagaku,* 2004, K. P. C. Vollhardt, Kagakudojin).

The partial structure represented by the formula (1) may be attached to the raw material monomer of the polymer of the present invention in advance, and polymerized to obtain the polymer of the present invention, as described above. Alternatively, the partial structure represented by formula (1) may be attached to the desired portion after synthesizing a portion corresponding to the main chain of the polymer of the present invention.

Known techniques may be used for the purification of the compound, including *Separation and Purification Technique Handbook* (*Bunri Seisei Gijyutsu Handbook,* 1993, Ed. The Chemical Society of Japan Foundation), *High Separation of Trace Components and Poorly Purifiable Substances by Chemical Transformation* (*Kagaku Henkanhou ni yoru Biryou Seibun oyobi Nannseisei Busshitsu no Koudo Seisei,* 1988, published by IPC), and the Separation and Purification section of *Laboratory Chemistry Course* (*Jikken Kagaku Kouza,* 4th Ed. 1, 1990, Ed. The Chemical Society of Japan Foundation). Specific methods include extraction (including suspension washing, boil washing, ultrasonic washing, and acid-base washing), adsorption, occlusion, melting, crystallization (including recrystallization from solvent, and repre- cipitation), distillation (ordinary pressure distillation, reduced pressure distillation), evaporation, sublimation (ordinary pressure sublimation, reduced pressure sublimation), ion exchange, dialysis, filtration, ultrafiltration, reverse osmosis, pressurized osmosis, zone melting, electrophoresis, centrifugation, floatation separation, precipitation separation, magnetic separation, and various chromatography techniques (classification by shape: column, paper, thin layer, capillary; classification by mobile phase: gas, liquid, micelle, supercritical fluid; separation mechanism: adsorption, distribution, ion exchange, molecular sieve, chelate, gel filtration, exclusion, and affinity).

The following techniques and devices may be used for the confirmation of the product, and purity analysis, as required. Gas chromatography (GC), high-performance liquid chromatography (HPLC), high-speed amino acid analyzer (organic compound), capillary electrophoresis (CE), size exclusion chromatography (SEC), gel permeation chromatography (GPC), cross fractionation chromatography (CFC), mass spectrometry (MS, LC/MS, GC/MS, MS/MS), nuclear magnetic resonance devices (NMR; $^1$H NMR, $^{13}$C NMR), a Fourier transformation infrared spectrometer (FT-IR), ultraviolet-visible-near-infrared spectrometers (UV, VIS, NIR), an electron spin resonance device (ESR), a transmission electron microscope (TEM-EDX), an electron probe microanalyzer (EPMA), a metallic element analyses (ion chromatography, inductively coupled plasma atomic emission spectroscopy (ICP-AES), atomic absorption spectrometry (AAS), x-ray fluorescence analysis device (XRF)), nonmetallic element analysis, and trace component analyses (ICP-MS, GF-AAS, GD-MS).

[Composition for Organic Electroluminescent Elements]

A composition for organic electroluminescent elements of the present invention contains the polymer of the present invention. The composition for organic electroluminescent elements of the present invention may contain only one kind of the polymer of the present invention, or may contain two or more kinds of the polymer of the present invention in any combination at any proportions.

{Polymer Content}

The content of the polymer of the present invention in the composition for organic electroluminescent elements of the present invention is typically 0.01 to 70 mass %, preferably 0.1 to 60 mass %, further preferably 0.5 to 50 mass %.

These ranges are preferable because defects and thickness nonuniformity are unlikely to occur in the organic layer formed.

The composition for organic electroluminescent elements according to the present invention may contain a solvent or other component, in addition to the polymer according to the present invention.

{Solvent}

The composition for organic electroluminescent elements of the present invention typically contains a solvent. Preferably, the solvent dissolves the polymer of the present invention. Specifically, the solvent is preferably one that dissolves typically 0.05 mass % or more, preferably 0.5 mass % or more, further preferably 1 mass % or more of the polymer of the present invention at room temperature.

Specific examples of the solvent include organic solvents, including:

aromatic solvents such as toluene, xylene, mesitylene, and cyclohexylbenzene; halogen-containing solvents such as 1,2-dichloroethane, chlorobenzene, and o-dichlorobenzene;

ether-based solvents such as aliphatic ethers (such as ethylene glycol dimethyl ether, ethylene glycol diethyl ether, and propylene glycol-1-monomethyl ether acetate (PG-MEA)), and aromatic ethers (such as 1,2-dimethoxybenzene, 1,3-dimethoxybenzene, anisole, phenetole, 2-methoxytoluene, 3-methoxytoluene, 4-methoxytoluene, 2,3-dimethyl anisole, and 2,4-dimethylanisole;

aliphatic esters such as ethyl acetate, n-butyl acetate, ethyl lactate, and n-butyl lactate; and ester-based solvents such as aromatic esters (such as phenyl acetate, phenyl propionate, methyl benzoate, ethyl benzoate, isopropyl benzoate, propyl benzoate, and n-butyl benzoate).

Other examples of the solvent include organic solvents used for compositions for forming a hole injection layer (described later), and organic solvents used for compositions for forming a hole transport layer (described later).

The solvent may be used alone, or in any combination of two or more at any proportions.

The solvent contained in the composition for organic electroluminescent elements of the present invention is preferably a solvent having a surface tension at 20° C. of typically less than 40 dyn/cm, preferably 36 dyn/cm or less, more preferably 33 dyn/cm or less.

When the composition for organic electroluminescent elements of the present invention is used to form a coating film by using a wet film formation method, and the polymer of the present invention is crosslinked to form an organic layer, it is preferable that the solvent has good compatibility with the underlying base. This is because the uniformity of film quality greatly affects the uniformity and stability of the emission by the organic electroluminescent element. When using a wet film formation method, the composition for organic electroluminescent elements is thus required to have a low surface tension so that a more level, uniform coating film can be formed. Use of a solvent having a low surface tension such as above is preferable because it enables forming a uniform layer containing the polymer of the present invention, and, in turn, forming a uniform crosslink layer.

Specific examples of low-surface-tension solvents include aromatic solvents such as toluene, xylene, mesitylene, and cyclohexylbenzene; ester-based solvents such as ethyl benzoate; ether-based solvents such as anisole; trifluoromethoxyanisole, pentafluoromethoxybenzene, 3-(trifluoromethyl)anisole, and ethyl(pentafluorobenzoate).

On the other hand, it is preferable that the solvent contained in the composition for organic electroluminescent elements of the present invention have a vapor pressure at 25° C. of typically 10 mmHg or less, preferably 5 mmHg or less, and typically 0.1 mmHg or more. With such a solvent, it is possible to prepare a composition for organic electroluminescent elements that is preferable for the process of producing the organic electroluminescent element using a wet film formation method, and that is suited for the characteristics of the polymer of the present invention.

Specific examples of such solvents include aromatic solvents such as toluene, xylene, and mesitylene; ether-based solvents; and ester-based solvents.

Moisture has a possibility of causing a performance drop in the organic electroluminescent element, and, particularly, accelerating a luminance drop during continuous driving. It is therefore preferable that the solvent have a solubility for water at 25° C. of preferably 1 mass % or less, more preferably 0.1 mass % or less so that the amount of residual moisture can be reduced as much as possible during the wet film formation.

The content of the solvent contained in the composition for organic electroluminescent elements of the present invention is typically 10 mass % or more, preferably 30 mass % or more, more preferably 50 mass % or more, particularly preferably 80 mass % or more. With a solvent content at or above these lower limits, the layer formed can have desirable flatness and uniformity.

<Electron-Accepting Compound>

When used to form a hole injection layer, it is preferable for low resistance that the composition for organic electroluminescent elements of the present invention further contain an electron-accepting compound.

The electron-accepting compound is preferably a compound having oxidative power, and capable of accepting an electron from the polymer of the present invention. Specifically, the electron-accepting compound is a compound with an electron affinity of preferably 4 eV or more, further preferably 5 eV or more.

Examples of such electron-accepting compounds include one or more compounds selected from the group consisting of triaryl boron compounds, halogenated metals, Lewis acids, organic acids, onium salts, salts of an arylamine and a halogenated metal, and salts of an arylamine and a Lewis acid.

Specific examples include onium salts with a substituted organic group, such as 4-isopropyl-4'-methyldiphenyliodonium tetrakis(pentafluorophenyl)borate, and triphenylsulfonium tetrafluoroborate (WO2005/089024); high-valence inorganic compounds such as iron(III) chloride (JP-A-11-251067), and ammonium peroxodisulfate; cyano compounds such as tetracyanoethylene; aromatic boron compounds such as tris(pentafluorophenyl)borane (JP-A-2003-31365); fullerene derivatives; and iodine.

The composition for organic electroluminescent elements of the present invention may contain the electron-accepting compound either alone, or in any combination of two or more at any proportions.

When the composition for organic electroluminescent elements of the present invention contains an electron-accepting compound, the content of the electron-accepting compound in the composition for organic electroluminescent elements of the present invention is typically 0.0005 mass % or more, preferably 0.001 mass % or more, and typically 20 mass % or less, preferably 10 mass % or less. The proportion of the electron-accepting compound with respect to the polymer of the present invention in the composition for organic electroluminescent elements is typically 0.5 mass % or more, preferably 1 mass % or more, more preferably 3 mass % or more, and typically 80 mass % or less, preferably 60 mass % or less, further preferably 40 mass % or less.

The content of the electron-accepting compound in the composition for organic electroluminescent elements is preferably at or above the foregoing lower limits because it allows the electron receptor to accept electrons from the polymer, and lowers the resistance of the organic layer formed. The content is preferably at or below the foregoing upper limits because defects and thickness nonuniformity are unlikely to occur in the organic layer formed.

The composition for organic electroluminescent elements of the present invention may further contain a cationic radical compound.

The cationic radical compound is preferably an ionic compound composed of a cationic radical and a counter anion, the former being a chemical species resulting from the removal of an electron from a hole-transporting compound. Note, however, that, when the cationic radical is derived from a hole transporting polymer compound, the cationic radical has a structure resulting from the removal of an electron from the repeating unit of the polymer compound.

The cationic radical is preferably a chemical species that results from the removal of an electron from a hole-transporting compound such as above. The cationic radical is preferably a chemical species that results from the removal of an electron from a compound preferred as a hole-transporting compound for reasons such as amorphous property, transmittance for visible light, heat resistance, and solubility.

The cationic radical compound may be produced by mixing the hole-transporting compound and the electron-accepting compound. Specifically, electron migration from the hole-transporting compound to the electron-accepting compound occurs upon mixing the hole-transporting compound and the electron-accepting compound, and this produces a cationic compound composed of a cationic radical of the hole-transporting compound, and a counter anion.

When the composition for organic electroluminescent elements of the present invention contains a cationic radical compound, the content of the cationic radical compound in the composition for organic electroluminescent elements of the present invention is typically 0.0005 mass % or more, preferably 0.001 mass % or more, and typically 40 mass % or less, preferably 20 mass % or less. The content of the cationic radical compound is preferably at or above these lower limits because it lowers the resistance of the organic layer formed. The content is preferably at or below the foregoing upper limits because defects and thickness non-uniformity are unlikely to occur in the organic layer formed.

[Organic Electroluminescent Element]

An organic electroluminescent element of the present invention is preferably an organic electroluminescent element that includes a substrate, an anode and a cathode provided on the substrate, and an organic layer provided between the anode and the cathode, and in which the organic layer is a layer formed with the composition for organic electroluminescent elements of the present invention containing the polymer of the present invention, using a wet film formation method.

In the organic electroluminescent element of the present invention, the layer formed by using a wet film formation method is preferably at least one of a hole injection layer and a hole transport layer. Preferably, the organic layer is a layer that includes a hole injection layer, a hole transport layer, and a light-emitting layer, and in which the hole injection layer, the hole transport layer, and the light-emitting layer are all formed by using a wet film formation method.

As used herein, "wet film formation method" refers to a deposition method that forms a coating by using a wet coating method, for example, such as spin coating, dip coating, die coating, bar coating, blade coating, roll coating, spray coating, capillary coating, an inkjet method, nozzle printing, screen printing, gravure printing, and flexography, and that forms a film upon drying the coating. The deposition method is preferably, for example, spin coating, spray coating, an inkjet method, and nozzle printing.

An embodiment of the organic electroluminescent element of the present invention, including the layer configuration, and a typical method for forming the layers, is described below with reference to the FIGURE.

The FIGURE is a schematic view of a cross section representing an example of the structure of an organic electroluminescent element 10 of the present invention. Referring to the FIGURE, the organic electroluminescent element 10 includes a substrate 1, an anode 2, a hole injection layer 3, a hole transport layer 4, a light-emitting layer 5, a hole blocking layer 6, an electron transport layer 7, an electron injection layer 8, and a cathode 9. The materials used for these structures are not particularly limited, and known materials may be used. The following descriptions will be given through the case of using materials and methods commonly used for these layers, though materials and methods are not particularly limited. It is intended that the content of any patent publications and journals cited herein may be appropriately applied or used within the common knowledge of a person skilled in the art.

{Substrate}

The substrate 1 serves as a support for the organic electroluminescent element, and is typically a quartz or glass plate, a metal board or a metal foil, or a plastic film or sheet. Preferably, the substrate 1 is a glass plate, or a transparent synthetic resin plate of, for example, polyester, polymethacrylate, polycarbonate, or polysulfone. The substrate is preferably made of a material with a good gas barrier property to prevent deterioration of the organic electroluminescent element due to ambient air. When using a material with a poor gas barrier property such as a synthetic resin substrate, it is therefore preferable to improve the gas barrier property by providing a dense silicon oxide film or the like on at least one side of the substrate.

{Anode}

The anode 2 functions to inject holes into the layer on the light-emitting layer 5 side.

The anode 2 is typically configured from metals such as aluminum, gold, silver, nickel, palladium, and platinum; metal oxides such as indium and/or tin oxide; halogenated metals such as copper iodide; and conductive polymers such as carbon black, poly(3-methylthiophene), polypyrrole, and polyaniline.

The anode 2 is typically formed by using a dry method such as sputtering, and vacuum vapor deposition. When the anode is formed by using materials such as metallic fine particles of silver, fine particles of copper iodide, carbon black, fine particles of conductive metal oxides, and a fine powder of conductive polymers, the anode may be formed by being applied to the substrate after being dispersed in a suitable binder resin solution. In the case of a conductive polymer, the anode may be formed by directly forming a thin film on a substrate through electropolymerization, or applying a conductive polymer on a substrate (Appl. Phys. Lett., Vol. 60, p. 2711, 1992).

The anode 2 typically has a monolayer structure, but may have a laminate structure, as appropriate. When the anode 2 has a laminate structure, a different conductive material may be laminated on the first anode layer.

The thickness of the anode 2 may be determined according to factors such as the required transparency, and the material used. When high transparency is required, it is preferable that the anode 2 have a thickness that makes the visible light transmittance 60% or more, further preferably 80% or more. The thickness of the anode 2 is typically 5 nm or more, preferably 10 nm or more, and typically 1,000 nm or less, preferably 500 nm or less. On the other hand, when transparency is not required, the anode 2 may have any thickness as may be required for the required strength or other requirements. In this case, the anode 2 may have the same thickness as the substrate.

When other layers are deposited on the surface of the anode 2, it is preferable to treat the anode surface with, for example, ultraviolet light/ozone, an oxygen plasma, or an argon plasma before depositing layers, in order to remove impurities on the anode 2, and adjust the ionization potential for improved hole injecting ability.

{Hole Injection Layer}

The layer that serves to transport holes from the anode 2 side to the light-emitting layer 5 side is typically called hole injection-transport layer, or a hole transport layer. When there are two or more layers that serve to transport holes from the anode 2 side to the light-emitting layer 5 side, the layer closer or closest to the anode side may be called hole injection layer 3. It is preferable to form the hole injection layer 3 in terms of enhancing the hole transport function from the anode 2 to the light-emitting layer 5 side. When formed, the hole injection layer 3 is typically formed on the anode 2.

The hole injection layer 3 has a thickness of typically 1 nm or more, preferably 5 nm or more, and typically 1,000 nm or less, preferably 500 nm or less.

The hole injection layer may be formed by using a vacuum vapor deposition method or a wet film formation method. For ease of deposition, it is preferable to form the hole injection layer by using a wet film formation method.

The hole injection layer 3 preferably contains a hole-transporting compound, more preferably a hole-transporting compound and an electron-accepting compound. Further preferably, a cationic radical compound is contained in the hole injection layer. Particularly preferably, a cationic radical compound and a hole-transporting compound are contained in the hole injection layer.

The following describes a typical method of forming the hole injection layer. However, in the organic electroluminescent element of the present invention, the hole injection layer is preferably formed by using a wet film formation method, using the composition for organic electroluminescent elements of the present invention.

<Hole-Transporting Compound>

A composition for forming the hole injection layer typically contains a hole-transporting compound that becomes the hole injection layer 3. In the case of a wet film formation method, a composition for forming the hole injection layer also contains a solvent. A composition for forming the hole injection layer is preferably a composition having high hole transporting ability, and that can efficiently transport the injected holes. It is therefore preferable that the composition have high hole mobility, and do not easily generate trapping impurities during the production or use. It is also preferable that the composition have desirable stability, small ionization potential, and high transparency for visible light. When the hole injection layer is in contact with the light-emitting layer, it is preferable that the composition do not quench the emission from the light-emitting layer, or form an exciplex with the light-emitting layer, and lower the emission efficiency.

The hole injection layer 3 preferably contains the electron-accepting compound, and/or the cationic radical compound, so that the conductivity of the hole injection layer can improve upon oxidation of the hole-transporting compound.

Polymer compound-derived cationic radical compounds such as PEDOT/PSS (Adv. Mater., 2000, Vol. 12, p. 481), and emeraldine hydrochloride (J. Phys. Chem., 1990, Vol. 94, p. 7716) also generate through oxidative polymerization (dehydrogenation polymerization).

Here, oxidative polymerization means oxidation of a monomer that takes place either chemically with a persulfate or the like in an acidic solution, or electrochemically in an acidic solution. In the case of oxidative polymerization (dehydrogenation polymerization), a monomer is oxidized to form a polymer, and a cationic radical is produced after the removal of an electron from the polymer repeating unit with the anion derived from an acidic solution serving as a counter anion.

<Formation of Hole Injection Layer by Wet Film Formation Method>

When the hole injection layer 3 is formed by using a wet film formation method, a material of the hole injection layer is typically mixed with a soluble solvent (a solvent for the hole injection layer) to prepare a deposition composition (a composition for forming the hole injection layer). The composition for forming the hole injection layer is then applied and deposited onto the layer (typically, the anode) representing an underlayer of the hole injection layer, and dried to form the hole injection layer 3.

The hole-transporting compound in the composition for forming the hole injection layer may have any concentration, provided that it is not detrimental to the effects of the present invention. However, lower concentrations are preferred in terms of thickness uniformity, whereas higher concentrations are preferred from the standpoint of preventing defects in the hole injection layer. Specifically, the concentration is preferably 0.01 mass % or more, further preferably 0.1 mass % or more, particularly preferably 0.5 mass % or more, and preferably 70 mass % or less, further preferably 60 mass % or less, particularly preferably 50 mass % or less.

Examples of the solvent include ether-based solvents, ester-based solvents, aromatic hydrocarbon solvents, and amide-based solvents.

Examples of the ether-based solvents include aliphatic ethers such as ethylene glycol dimethyl ether, ethylene glycol diethyl ether, propylene glycol-1-monomethyl ether acetate (PGMEA); and aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole.

Examples of the ester-based solvents include aromatic esters such as phenyl acetate, phenyl propionate, methyl benzoate, ethyl benzoate, propyl benzoate, and n-butyl benzoate.

Examples of the aromatic hydrocarbon solvents include toluene, xylene, cyclohexylbenzene, 3-isopropylbiphenyl, 1,2,3,4-tetramethylbenzene, 1,4-diisopropylbenzene, cyclohexylbenzene, and methylnaphthalene. Examples of the amide-based solvents include N,N-dimethylformamide, and N,N-dimethylacetamide.

Other solvents, including dimethyl sulfoxide, also may be used.

The formation of the hole injection layer 3 by a wet film formation method typically begins with preparation of a composition for forming the hole injection layer, and the composition is applied and deposited on the layer (typically, the anode 2) representing an underlayer of the hole injection layer 3, and dried.

Typically, the applied film of the hole injection layer 3 is dried by methods such as heating, and drying under reduced pressure after being deposited. For example, methods of related art, such as that disclosed in JP-A-2009-212510, may be used.

<Formation of Hole Injection Layer by Vacuum Vapor Deposition Method>

When the hole injection layer 3 is formed by using a vacuum vapor deposition method, one or more constituent materials (for example, the hole-transporting compound, the electron-accepting compound) of the hole injection layer 3 are typically placed in a crucible installed inside a vacuum chamber (typically in different crucibles when two or more materials are used). After evacuating inside of the vacuum chamber to about $10^{-4}$ Pa with a vacuum pump, the crucible is heated (typically, each crucible is heated when two or more materials are used), and the material inside the crucible is evaporated while controlling the amount of evaporation (typically, while independently controlling the evaporation amount when two or more materials are used) to form the hole injection layer on the anode formed on the substrate placed opposite the crucible. When two or more materials are used, a mixture of these materials may be charged into a crucible, and heated and evaporated to form the hole injection layer. The vacuum vapor deposition method may be one commonly used in the art.

The hole injection layer 3 may be crosslinked as in the hole transport layer 4 descried below.

{Hole Transport Layer}

The hole transport layer 4 is a layer that serves to transport holes from the anode 2 side to the light-emitting layer 5 side. The hole transport layer 4 is not an essential layer of the organic electroluminescent element of the present invention. However, it is preferable to form the hole transport layer 4 in terms of enhancing the hole transport function from the anode 2 to the light-emitting layer 5. When formed, the hole transport layer 4 is typically formed between the anode 2 and the light-emitting layer 5. When the hole injection layer 3 is present, the hole transport layer 4 is formed between the hole injection layer 3 and the light-emitting layer 5.

The hole transport layer 4 has a thickness of typically 5 nm or more, preferably 10 nm or more, and typically 300 nm or less, preferably 100 nm or less.

The hole transport layer 4 may be formed by using a vacuum vapor deposition method or a wet film formation method. For ease of deposition, it is preferable to form the hole transport layer 4 by using a wet film formation method.

The following describes a typical method of forming the hole transport layer. However, in the organic electroluminescent element of the present invention, the hole transport layer is preferably formed by using a wet film formation method, using the composition for organic electroluminescent elements of the present invention.

The hole transport layer 4 typically contains a hole-transporting compound. Examples of the hole-transporting compound contained in the hole transport layer 4 include:

aromatic diamines containing two or more tertiary amines, and in which two or more fused aromatic rings are substituted with nitrogen atoms, such as 4,4'-bis[N-(1-naphthyl)-N-phenylamino]biphenyl (JP-A-5-234681);

aromatic amine compounds having a starburst structure, for example, such as 4,4',4''-tris(1-naphthylphenylamino) triphenylamine (J. Lumin., Vol. 72-74, p. 985, 1997);

aromatic amine compounds composed of a tetramer of triphenylamine (Chem. Commun., p. 2175, 1996);

spiro compounds, for example, such as 2,2',7,7'-tetrakis-(diphenylamino)-9,9'-spirobifluorene (Synth. Metals, Vol. 91, p. 209, 1997); and carbazole derivatives such as 4,4'-N,N'-dicarbazolebiphenyl.

Also preferred for use are, for example, polyvinylcarbazole, polyvinyltriphenylamine (JP-A-7-53953), and polyarylene ether sulfone containing tetraphenylbenzidine (Polym. Adv. Tech., Vol. 7, p. 33, 1996).

<Formation of Hole Transport Layer by Wet Film Formation Method>

When the hole transport layer is formed by using a wet film formation method, the hole transport layer is typically formed in the same manner as in forming the hole injection layer using a wet film formation method, except that the composition for forming the hole injection layer is replaced with a composition for forming the hole transport layer.

When the hole transport layer is formed by using a wet film formation method, the composition for forming the hole transport layer typically also contains a solvent. The solvent used for the composition for forming the hole transport layer may be the same solvent used for the composition for forming the hole injection layer above.

The hole-transporting compound in the composition for forming the hole transport layer may be contained in the same concentration range as that of the hole-transporting compound contained in the composition for forming the hole injection layer.

The formation of the hole transport layer by a wet film formation method may be performed in the same manner as described in the deposition method of the hole injection layer.

<Formation of Hole Transport Layer by Vacuum Vapor Deposition Method>

When using a vacuum vapor deposition method to form the hole transport layer, the hole transport layer may typically be formed in the same manner as in the formation of the hole injection layer by a vacuum vapor deposition method, except that the composition for forming the hole injection layer is replaced with a composition for forming the hole transport layer. The deposition conditions, including the vacuum degree of vapor deposition, the deposition rate, and the temperature may be the same as those used in the vacuum vapor deposition of the hole injection layer.

{Light-Emitting Layer}

The light-emitting layer 5 is a layer that serves to emit light upon being excited by the recombination of the injected holes from the anode 2 and the injected electrons from the cathode 9 in response to an applied electric field between a pair of electrodes. The light-emitting layer 5 is a layer formed between the anode 2 and the cathode 9, and is formed between the hole injection layer and the cathode when the hole injection layer is present on the anode, and between the hole transport layer and the cathode when the hole transport layer is present on the anode.

The light-emitting layer 5 may have any thickness, provided that it is not detrimental to the effects of the present invention. However, it is preferable that the light-emitting layer 5 be thicker from the standpoint of preventing defects in the film, and thinner in terms of more easily achieving a low drive voltage. For these reasons, the thickness is preferably 3 nm or more, further preferably 5 nm or more, and typically 200 nm or less, further preferably 100 nm or less.

The light-emitting layer 5 contains at least a material having a light-emitting property (light-emitting material), preferably with a material having a charge-transporting property (charge-transporting material).

<Light-Emitting Material>

The light-emitting material is not particularly limited, and a known light-emitting material may be used, as long as it emits light at the desired emission wavelengths, and is not detrimental to the effects of the present invention. The light-emitting material may be a fluorescent material, or a phosphorescent material. Preferably, the light-emitting material is a material having desirable emission efficiency, and a phosphorescent material is preferred in terms of internal quantum efficiency.

Examples of the fluorescent material include:

fluorescent materials that produce blue emission (blue fluorescent material), for example, such as naphthalene, perylene, pyrene, anthracene, coumalin, chrysene, p-bis(2-phenylethenyl)benzene, and derivatives thereof; and fluorescent materials that produce green emission (green fluorescent material), for example, such as quinacridone derivatives, coumalin derivatives, and aluminum complexes such as $Al(C_9H_6NO)_3$.

Examples of fluorescent materials that produce yellow emission (yellow fluorescent material) include rubrene, and perimidone derivatives.

Examples of fluorescent materials that produce red emission (red fluorescent material) include DCM (4-(dicyanomethylene)-2-methyl-6-(p-dimethylaminostyryl)-4H-pyran)- based compounds, benzopyran derivatives, rhodamine derivatives, benzothioxanthene derivatives, and azabenzothioxanthene.

The phosphorescent material may be, for example, an organometallic complex containing a metal selected from Group 7 to 11 of the long-form periodic table. Preferred examples of the metals selected from Group 7 to 11 of the periodic table include ruthenium, rhodium, palladium, silver, rhenium, osmium, iridium, platinum, and gold.

The ligand of the organometallic complex is preferably a ligand in which a (hetero)aryl group is joined to pyridine, pyrazole, or phenanthroline, for example, such as a (hetero)arylpyridine ligand, and a (hetero)arylpyrazole ligand, particularly preferably a phenylpyridine ligand, and a phenylpyrazole ligand. Here, (hetero)aryl means an aryl group or a heteroaryl group.

Specifically, preferred examples of the phosphorescent material include phenylpyridine complexes such as tris(2-phenylpyridine)iridium, tris(2-phenylpyridine)ruthenium, tris(2-phenylpyridine)palladium, bis(2-phenylpyridine)platinum, tris(2-phenylpyridine)osmium, and tris(2-phenylpyridine)rhenium; and porphyrin complexes such as platinum octaethylporphyrin, platinum octaphenylporphyrin, palladium octaethylporphyrin, and palladium octaphenylporphyrin.

Examples of the polymeric light-emitting material include polyfluorene-based materials such as poly(9,9-dioctylfluorene-2,7-diyl), poly[(9,9-dioctylfluorene-2,7-diyl)-co-(4,4'-(N-(4-sec-butylphenyl))diphenylamine)], and poly[(9,9-dioctylfluorene-2,7-diyl)-co-(1,4-benzo-2{2,1'-3}-triazole)]; and polyphenylene vinylene-based materials such as poly[2-methoxy-5-(2-ethylhexyloxy)-1,4-phenylenevinylene].

<Charge-Transporting Material>

The charge-transporting material is a material having positive-charge (hole) or negative-charge (electron) transporting ability. The charge-transporting material is not particularly limited, and known light-emitting materials may be used, provided that it is not detrimental to the effects of the present invention.

The charge-transporting material may be a compound conventionally used for light-emitting layers of organic electroluminescent elements, and is preferably a compound used as a host material of light-emitting layers.

Specific examples of the charge-transporting material include compounds exemplified as the hole-transporting compound of the hole injection layer, such as aromatic amine-based compounds, phthalocyanine-based compounds, porphyrin-based compounds, oligothiophene-based compounds, polythiophene-based compounds, benzylphenyl-based compounds, compounds in which tertiary amines are joined to each other with a fluorene group, hydrazone-based compounds, silazane-based compounds, silanamine-based compounds, phosphamine-based compounds, and quinacridone-based compounds; and electron transporting compounds such as anthracene-based compounds, pyrene-based compounds, carbazole-based compounds, pyridine-based compounds, phenanthroline-based compounds, oxadiazole-based compounds, and silole-based compounds.

Also preferred for use are compounds exemplified above as the hole-transporting compound of the hole transport layer, specifically, for example, aromatic diamines containing two or more tertiary amines, and in which two or more fused aromatic rings are substituted with nitrogen atoms, for example, such as 4,4'-bis[N-(1-naphthyl)-N-phenylamino]biphenyl (JP-A-5-234681); aromatic amine compounds having a starburst structure, for example, such as 4,4',4"-tris(1-naphthylphenylamino)triphenylamine (J. Lumin., Vol. 72-74, p. 985, 1997); aromatic amine compounds composed of a tetramer of triphenylamine (Chem. Commun., p. 2175, 1996); fluorene-based compounds, for example, such as 2,2',7,7'-tetrakis-(diphenylamino)-9,9'-spirobifluorene (Synth. Metals, Vol. 91, p. 209, 1997); and carbazole-based compounds such as 4,4'-N,N'-dicarbazolebiphenyl.

Other examples include oxadiazole-based compounds such as 2-(4-biphenylyl)-5-(p-tert-butylphenyl)-1,3,4-oxadiazole (tBu-PBD), and 2,5-bis(1-naphthyl)-1,3,4-oxadiazole (BND); silole-based compounds such as 2,5-bis(6'-(2',2"-bipyridyl))-1,1-dimethyl-3,4-diphenylsilole (PyPySPyPy); and phenanthroline-based compounds such as bathophenanthroline (BPhen), and 2,9-dimethyl-4,7-diphenyl-1,10-phenanthroline (BCP, bathocuproin).

<Formation of Light-Emitting Layer by Wet Film Formation Method>

The light-emitting layer may be formed by using a vacuum vapor deposition method or a wet film formation method. For ease of deposition, a wet film formation method is preferred, and spin coating, and an inkjet method are further preferred. A wet film formation method is particularly preferred when the composition for organic electroluminescent elements of the present invention is used to form the hole injection layer or the hole transport layer as an underlayer of the light-emitting layer because the lamination is easier with a wet film formation method. When using a wet film formation method, the light-emitting layer is formed in the same manner as in the formation of the hole injection layer by a wet film formation method, except that the composition for forming the hole injection layer is replaced with a composition for forming the light-emitting layer prepared by mixing a light-emitting layer material with a soluble solvent (a solvent for the light-emitting layer).

The solvent may be, for example, any of the solvents exemplified above for the formation of the hole injection layer, including ether-based solvents, ester-based solvents, aromatic hydrocarbon solvents, and amide-based solvents. Other examples of the solvent include alkane-based solvents, halogenated aromatic hydrocarbon solvents, aliphatic alcohol solvents, alicyclic alcohol solvents, aliphatic ketone solvents, and alicyclic ketone solvents. Particularly preferred are alkane-based solvents, and aromatic hydrocarbon solvents.

{Hole Blocking Layer}

The hole blocking layer 6 may be provided between the light-emitting layer 5 and the electron injection layer 8 (described later). The hole blocking layer 6 is a layer that is laminated on the light-emitting layer 5, in contact with the interface with the light-emitting layer 5 on the cathode 9 side.

The hole blocking layer 6 serves to block the incoming holes from the anode 2 so that the holes doe not reach the cathode 9, and to efficiently transport the injected electrons from the cathode 9 toward the light-emitting layer 5. The material forming the hole blocking layer 6 is required to have properties such as high electron mobility, low hole mobility, a large energy gap (the difference between HOMO and LUMO), and a high excited triplet level (Ti).

Examples of hole blocking layer materials that satisfy such conditions include: mixed ligand complexes such as bis(2-methyl-8-quinolinolate)(phenolate)aluminum, and bis(2-methyl-8-quinolinolate)(triphenylsilanolate)aluminum; metal complexes such as a bis(2-methyl-8-quinolate)aluminum-μ-oxo-bis-(2-methyl-8-quinolinato)aluminum dinuclear metal complex; styryl compounds such as distyryl biphenyl derivatives (JP-A-11-242996); triazole derivatives such as 3-(4-biphenylyl)-4-phenyl-5-(4-tert-butylphenyl)-1, 2,4-triazole (JP-A-7-41759); and phenanthroline derivatives such as bathocuproin (JP-A-10-79297).

Also preferred as the hole blocking layer material are compounds having at least one pyridine ring that is substituted at positions 2, 4, and 6, such as those described in WO2005/022962.

The method for forming the hole blocking layer 6 is not limited, and the hole blocking layer 6 may be formed by using various methods, including a wet film formation method, and a vapor deposition method.

The hole blocking layer 6 may have any thickness, provided that it is not detrimental to the effects of the present invention. The thickness of the hole blocking layer 6 is typically 0.3 nm or more, preferably 0.5 nm or more, and typically 100 nm or less, preferably 50 nm or less.

{Electron Transport Layer}

The electron transport layer 7 is provided between the light-emitting layer 5 and the electron injection layer 8 to further improve the current efficiency of the element.

The electron transport layer 7 is formed from a compound that is capable of efficiently transporting the injected electrons from the cathode 9 toward the light-emitting layer 5 between electrodes under applied electric field. The electron transporting compound used for the electron transport layer 7 needs to be a compound having high injection efficiency for electrons from the cathode 9 or the electron injection layer 8, and high electron mobility, and must be capable of efficiently transporting the injected electrons.

Specific examples of the electron transporting compound used for the electron transport layer include metal complexes (such as an aluminum complex of 8-hydroxyquinoline (JP-A-59-194393)), metal complexes of 10-hydroxybenzo[h]quinoline, oxadiazole derivatives, distyrylbiphenyl derivatives, silole derivatives, 3-hydroxyflavone metal complexes, 5-hydroxyflavone metal complexes, benzoxazole metal complexes, benzothiazole metal complexes, trisbenzimidazolyl benzene (U.S. Pat. No. 5,645,948), quinoxaline compounds (JP-A-6-207169), phenanthroline derivatives (JP-A-5-331459), 2-t-butyl-9,10-N,N'-dicyanoanthraquinonediimine, n-type hydrogenated amorphous silicon carbide, n-type zinc sulfide, and n-type zinc selenide.

The electron transport layer 7 has a thickness of typically 1 nm or more, preferably 5 nm or more, and typically 300 nm or less, preferably 100 nm or less.

The electron transport layer 7 is formed by being laminated on the hole blocking layer 6 using a wet film formation method or a vacuum vapor deposition method in the manner described above. Typically, a vacuum vapor deposition method is used.

{Electron Injection Layer}

The electron injection layer 8 serves to efficiently inject the injected electrons from the cathode 9 to the electron transport layer 7 or the light-emitting layer 5.

For efficient electron injection, the material forming the electron injection layer 8 is preferably a metal with a low work function. Examples of such metals include alkali metals such as sodium and cesium, and alkali earth metals such as barium and calcium. Typically, the thickness is preferably 0.1 nm to 5 nm.

It is also preferable to dope organic electron-transporting materials such as nitrogen-containing heterocyclic compounds (for example, bathophenanthroline), and metal complexes (such as an aluminum complex of 8-hydroxyquinoline) with alkali metals such as sodium, potassium, cesium, lithium, and rubidium (described in, for example, JP-A-10-270171, JP-A-2002-100478, and JP-A-2002-100482) because the doping improves the electron injecting ability and transporting ability, and, at the same time, the film quality.

The electron injection layer 8 has a thickness of typically 5 nm or more, preferably 10 nm or more, and typically 200 nm or less, preferably 100 nm or less.

The electron injection layer 8 is formed by being laminated on the light-emitting layer 5, or on the hole blocking layer 6 or the electron transport layer 7 formed on the light-emitting layer 5, using a wet film formation method or a vacuum vapor deposition method.

In the case of a wet film formation method, details are as described for the light-emitting layer.

{Cathode}

The cathode 9 serves to inject electrons to the layers (including the electron injection layer, and the light-emitting layer) on the light-emitting layer 5 side.

The material of the cathode 9 may be the same material used for the anode 2. For efficient electron injection, it is, however, preferable to use a metal with a low work function, for example, such as tin, magnesium, indium, calcium, aluminum, silver, and alloys of these metals. Specific examples include low-work-function alloy electrodes such as a magnesium-silver alloy, a magnesium-indium alloy, and an aluminum-lithium alloy.

For element stability, a metal layer having a high work function, and that is stable in the atmosphere is preferably laminated on the cathode to protect the cathode from the low-work-function metal. Examples of such laminated metals include aluminum, silver, copper, nickel, chromium, gold, and platinum.

The cathode typically has the same thickness as the anode.

{Other Layers}

The organic electroluminescent element of the present invention may have other layers, provided that these are not detrimental to the effects of the present invention. Specifically, any other layer may be provided between the anode and the cathode.

{Other Element Configurations}

The organic electroluminescent element of the present invention may have a reverse structure. Specifically, the cathode, the electron injection layer, the electron transport layer, the hole blocking layer, the light-emitting layer, the hole transport layer, the hole injection layer, and the anode may be laminated in this order on the substrate.

When used for an organic electroluminescent device, the organic electroluminescent element of the present invention may be used as a single organic electroluminescent element, or may be configured as an array of a plurality of organic electroluminescent elements, or may be configured with the anode and the cathode disposed in an X-Y matrix.

[Organic EL Display Device]

An organic electroluminescent display device (organic EL display device) of the present invention uses the organic electroluminescent element of the present invention. The type or structure of the organic EL display device of the present invention are not particularly limited, and the organic EL display device may be assembled according to an ordinary method using the organic electroluminescent element of the present invention.

For example, the organic EL display device of the present invention may be formed by using the method described in *Organic EL Display* (Ohmsha, published Aug. 20, 2004, Shizuo Tokito, Chihaya Adachi, Hideyuki Murata).

[Organic EL Lighting Device]

An organic electroluminescent lighting device (organic EL lighting device) of the present invention uses the organic electroluminescent element of the present invention. The type or structure of the organic EL lighting device of the present invention are not particularly limited, and the organic EL lighting device may be assembled according to an ordinary method using the organic electroluminescent element of the present invention.

EXAMPLES (Synthesis of Model Compound)

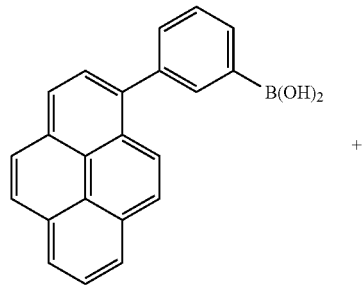

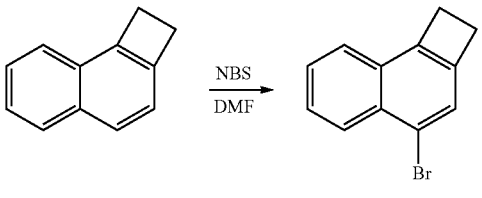

Compound 2

1.00 g (6.48 mmol) of 1,2-dihydrocyclobuta[a]naphthalene was dissolved in 15 ml of N,N-dimethylformamide, and a solution dissolving 1.15 g (6.48 mmol) of N-bromosuccinimide in 10 ml of N,N-dimethylformamide was dropped at room temperature. A reaction was allowed at room temperature for 98 h. After adding purified water to the reaction liquid, the mixture was separated with methylene chloride. The organic layer was concentrated, and purified by silica gel column chromatography (acetonitrile:tetrahydrofuran=9:1) to obtain compound 2 (0.56 g).

$^1$H-NMR (400 MHz, CDCl$_3$) δ 3.28 to 3.35 (m, 4H); 7.49 to 7.53 (m, 2H); 7.56 (s, 1H); 7.66 to 7.70 (m, 1H); 8.26 to 8.30 (m, 1H).

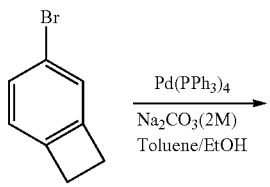

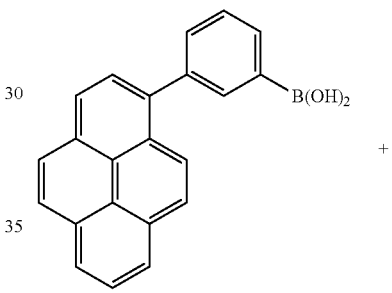

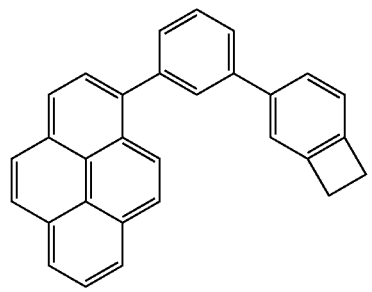

Compound 1

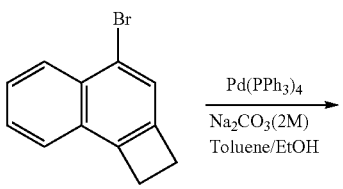

Compound 2

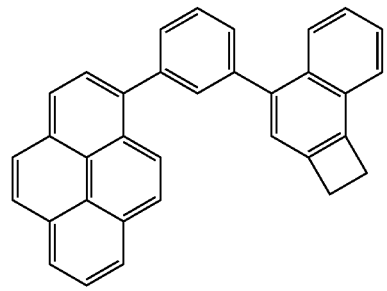

Compound 3

2.11 g (6.56 mmol) of 3-(1-pyrenyl)phenylboronic acid, 1.20 g (6.56 mmol) of 4-bromocyclobutene, toluene:ethanol (30 ml:15 ml), and 15 ml of a 2 M sodium carbonate aqueous solution were stirred for 40 min while being heated at 60° C. under a stream of nitrogen, and refluxed for 6 h after adding 0.15 g (0.13 mmol) of tetrakis(triphenylphosphine)palladium(0). After allowing the mixture to cool to room temperature, toluene (100 ml) and water (120 ml) were added to the reaction liquid, and the mixture was stirred and separated. The aqueous layer was then extracted with toluene (100 ml×2 times). With the organic layer, the mixture was dried over magnesium sulfate to concentrate. Compound 1 (1.80 g) was obtained after purification by silica gel column chromatography (hexane:ethyl acetate=9:1).

$^1$H-NMR (400 MHz, CDCl$_3$) δ 3.23 (s, 4H); 7.13 (d, 1H); 7.38 (s, 1H); 7.51 to 7.68 (m, 4H); 7.82 to 8.04 (m, 4H); 8.10 (s, 2H); 8.15 to 8.25 (m, 4H).

2.38 g (7.39 mmol) of 3-(1-pyrenyl)phenylboronic acid, 2.07 g (8.88 mmol) of compound 2, toluene:ethanol (60 ml:30 ml), and 22 ml of a 2 M sodium carbonate aqueous solution were stirred for 40 min while being heated at 60° C. under a stream of nitrogen, and refluxed for 3 h after adding 0.26 g (0.22 mmol) of tetrakis(triphenylphosphine)palladium(0). After allowing the mixture to cool to room temperature, toluene (200 ml) and water (240 ml) were added to the reaction liquid, and the mixture was stirred and separated. The aqueous layer was then extracted with toluene (100 ml×2 times). With the organic layer, the mixture was dried over magnesium sulfate to concentrate. Compound 3 (3.20 g) was obtained after purification by silica gel column chromatography (hexane:methylene chloride=6:1).

$^1$H-NMR (400 MHz, CDCl$_3$) δ 3.33 to 3.45 (m, 4H); 7.31 (s, 1H); 7.39 to 7.48 (m, 2H); 7.57 to 7.77 (m, 5H); 7.95 to 8.30 (m, 10H).

REFERENCE EXAMPLE

Heat generation, peaking at 262° C., due to crosslinking reaction was observed in differential scanning calorimetry (DSC) of compound 1 with a DSC-50 calorimeter manufactured by Shimadzu Corporation. Similarly, differential scanning calorimetry of compound 3 showed heat generation due to crosslinking reaction with a peak temperature of 235° C., 27° C. lower than the measurement result for compound 1.

There results confirmed that the 1,2-dihydrocyclobuta[a]naphthalene contained in compound 3 undergoes a crosslinking reaction at a temperature 27° C. below the crosslinking temperature of the benzocyclobutene contained in compound 1. It thus appears that the polymer of the present invention having 1,2-dihydrocyclobuta[a]naphthalene as a crosslink group would be insoluble for the solvent at lower temperatures than the crosslinking temperature of the conventional polymer having benzocyclobutene as a crosslink group.

(Monomer Synthesis)

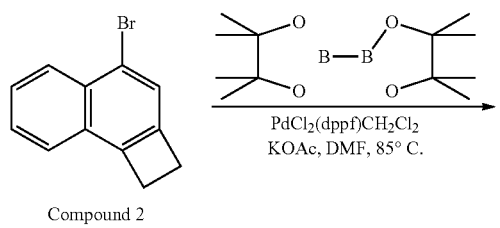

Compound 2

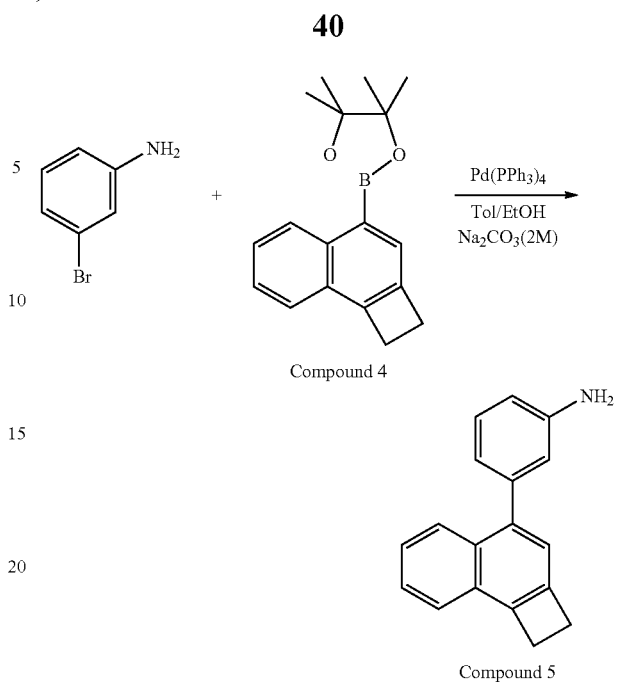

Compound 4

Compound 5

0.78 g (4.54 mmol) of 3-bromoaniline, 1.40 g (5.00 mmol) of compound 4, sodium carbonate (2.41 g, 22.7 mmol), 30 ml of toluene, 15 ml of ethanol, and 12 ml of water were heated to 65° C. under a stream of nitrogen. After adding tetrakis(triphenylphosphine)palladium (0.26 g, 0.23 mmol), the mixture was heated to reflux for 6 h under nitrogen. After being allowed to cool, the mixture was extracted with ethyl acetate, and the organic layer was dried over magnesium sulfate to concentrate. Compound 5 (0.59 g) was obtained upon purification by silica gel column chromatography (hexane:ethyl acetate=8:1).

Compound 4

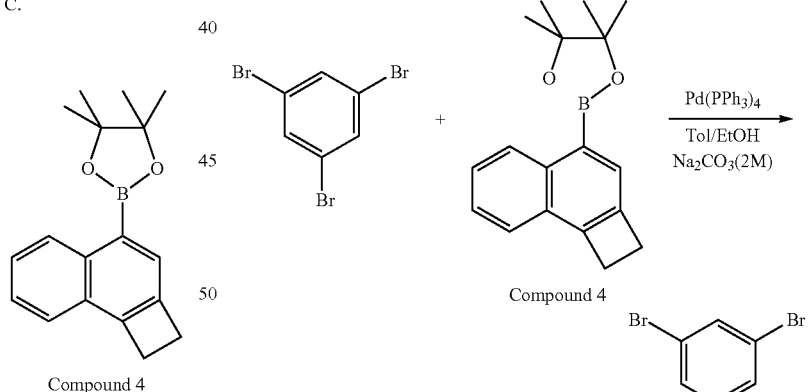

Compound 4

Compound 6

100 ml of dimethyl sulfoxide, 4.8 g (20.6 mmol) of compound 2, 5.75 g (22.7 mmol) of bis(pinacolato)diboron, and 6.1 g (61.8 mmol) of potassium acetate were stirred at 60° C. for 30 min under a stream of nitrogen. The mixture was stirred at 82° C. for 4 h after adding 0.51 g (0.62 mmol) of 1,1'-bis(diphenylphosphino)ferrocene palladium(II) dichloride dichloromethane. The reaction liquid was filtered under reduced pressure, and the filtrate was extracted with toluene, dried over anhydrous magnesium sulfate, and coarsely purified with activated earth. Compound 4 as a colorless solid product was obtained upon washing with acetonitrile (yield 4.0 g, percentage yield 69.3%).

3.00 g (9.53 mmol) of 1,3,5-tribromobenzene, 1.34 g (4.77 mmol) of compound 4, sodium carbonate (2.53 g, 23.85 mmol), 80 ml of toluene, 40 ml of ethanol, and 12 ml of water were heated to 65° C. under a stream of nitrogen.

After adding tetrakis(triphenylphosphine)palladium (0.11 g, 0.095 mmol), the mixture was heated to reflux for 4.5 h under nitrogen. After being allowed to cool, the mixture was extracted with toluene, and the organic layer was dried over magnesium sulfate to concentrate. Compound 6 (1.00 g) was obtained upon purification by silica gel column chromatography (hexane).

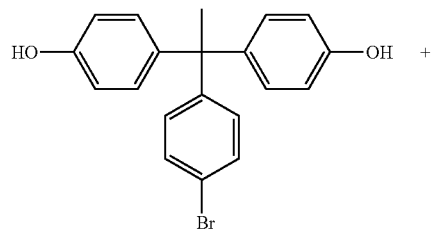

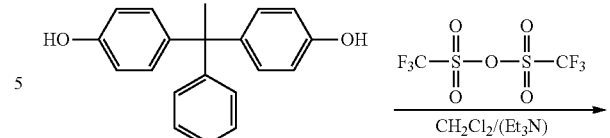

Compound 7

4.67 g (12.65 mmol) of 4,4'-[1-(4-bromophenyl)ethylidene]bisphenol, 3.90 g (13.92 mmol) of compound 4, and 80 ml of 1,2-dimethoxyethane were stirred at room temperature under a stream of nitrogen, and 22 ml of a 2 M potassium carbonate aqueous solution was added to the mixture. The mixture was then heated to reflux for 4 h after adding 0.29 g (0.25 mmol) of tetrakis(triphenylphosphine) palladium. After being allowed to cool, the mixture was extracted with ethyl acetate, and the organic layer was dried over magnesium sulfate to concentrate. Compound 7 (5.50 g) was obtained upon purification by silica gel column chromatography (hexane:ethyl acetate=3:1).

Compound 8

5.50 g (12.43 mmol) of compound 7 was dissolved in methylene chloride (90 ml), and 6.30 g (62.15 mmol) of triethylamine at −5° C., and a solution dissolving 10.5 g (37.3 mmol) of an trifluoromethanesulfonic anhydride in 17 ml of methylene chloride was dropped. The mixture was stirred for 4 h, and the reaction liquid was poured into ice water. The mixture was extracted with methylene chloride, and the organic layer was dried over magnesium sulfate to concentrate. Compound 8 (7.3 g) was obtained upon purification by silica gel column chromatography (hexane:methylene chloride=3:1).

Compound 8

-continued

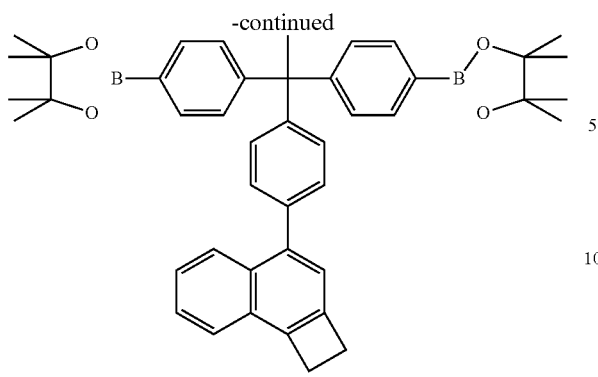

Compound 9

7.1 g (10.05 mmol) of compound 8, 6.1 g (24.11 mmol) of bis(pinacolato)diboron, 5.90 g (60.3 mmol) of potassium acetate, and 100 ml of dimethyl sulfoxide were stirred at 60° C. for 30 min under a stream of nitrogen. The mixture was stirred at 85° C. for 3.5 h after adding 0.41 g (0.50 mmol) of 1,1'-bis(diphenylphosphino)ferrocene palladium(II) dichloride dichloromethane. The reaction liquid was filtered under reduced pressure, and the filtrate was extracted with toluene. The organic layer was dried over anhydrous magnesium sulfate, and the filtrate was concentrated. After adding methanol, the precipitated colorless solid was filter off to obtain compound 9 (3.6 g).

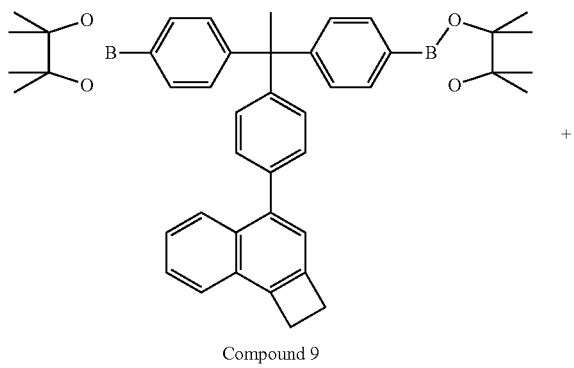

Compound 9

+

-continued

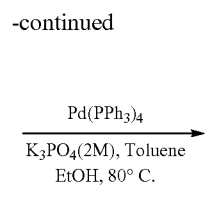

$$\xrightarrow{\text{Pd(PPh}_3)_4}{\text{K}_3\text{PO}_4(2\text{M}), \text{Toluene} \atop \text{EtOH, 80° C.}}$$

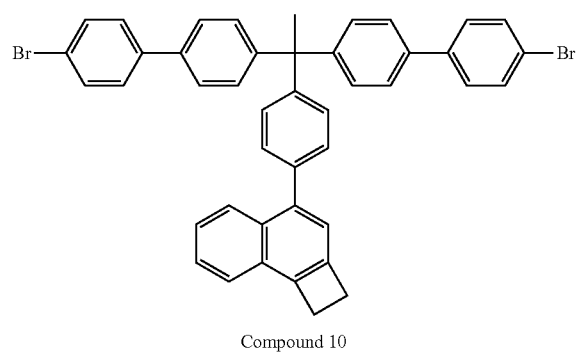

Compound 10

3.6 g (5.43 mmol) of compound 9, 3.38 g (11.96 mmol) of 1-bromo-4-iodobenzene, 120 ml of toluene, 60 ml of ethanol, and 18 ml of a 2 M potassium phosphate aqueous solution were mixed and heated, and stirred for 30 min under a stream of nitrogen. The mixture was refluxed for 4.5 h after adding 0.28 g (0.24 mmol) of tetrakis(triphenylphosphine) palladium. After adding water, the reaction liquid was extracted with toluene. Anhydrous magnesium sulfate and activated earth were added to the organic layer, and the filtrate was concentrated. Compound 10 (2.1 g) as a colorless solid product was obtained upon purification by adsorption silica gel column chromatography (developing solvent: n-hexane:toluene=4:1).

(Polymer Synthesis)

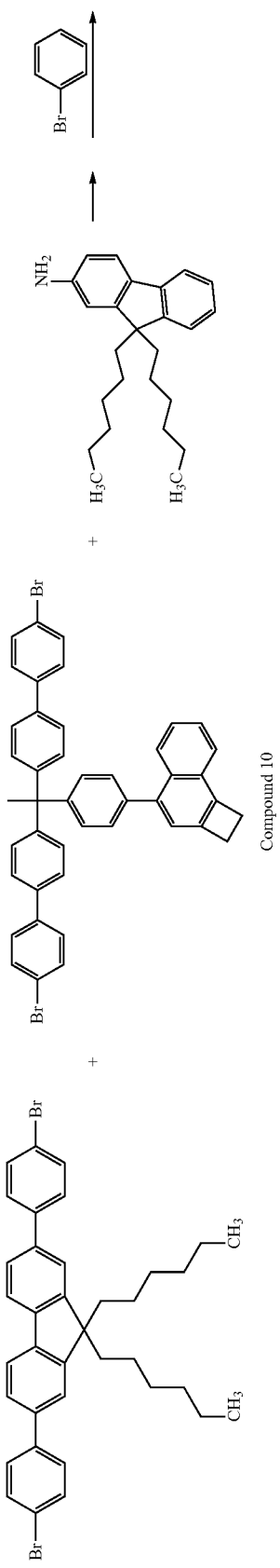
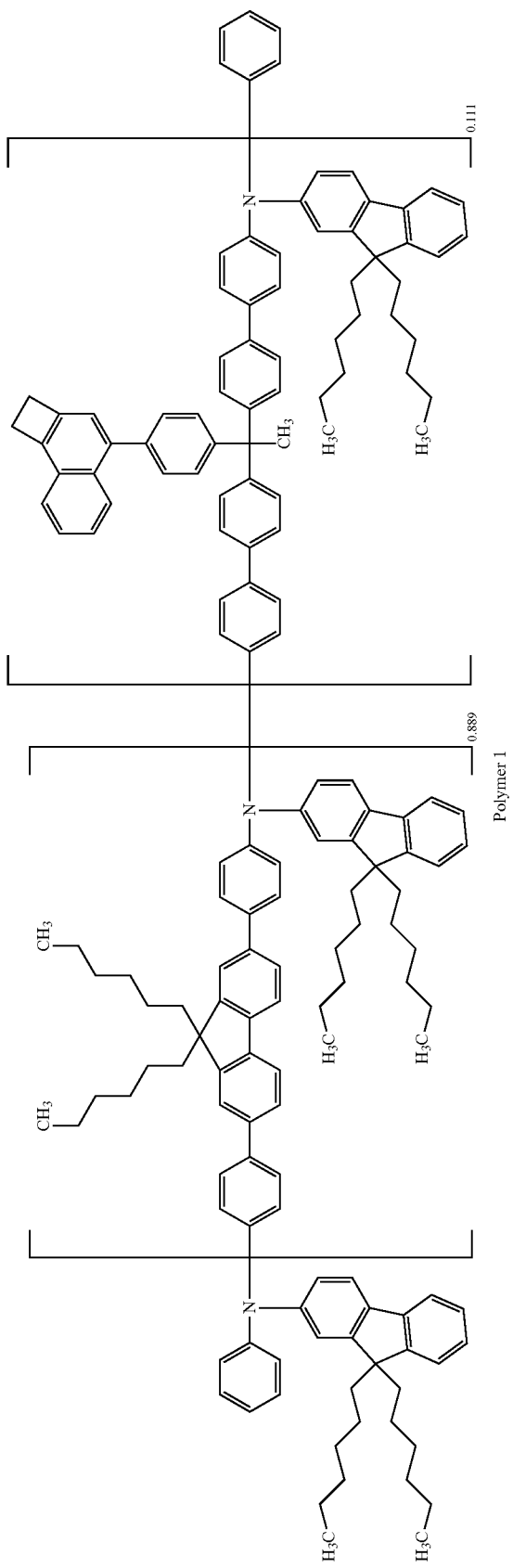
Compound 10
Polymer 1

2,7-bis(4-Bromophenyl)-9,9-dihexylfluorene (3.500 g, 5.43 mmol), 2-amino-9,9-dihexylfluorene (3.80 g, 10.87 mmol), tert-butoxysodium (4.02 g, 41.9 mmol), and toluene (80.7 ml) were charged into a system, and inside of the system was displaced with nitrogen before heating the mixture to 60° C. (solution A). [4-(N,N-Dimethylamino)phenyl]di-tert-butylphosphine (0.231 g, 0.868 mmol) was added to a 6.5-ml toluene solution of a tris(dibenzylideneacetone)dipalladium complex (0.100 g, 0.109 mmol), and the mixture was heated to 60° C. (solution B). Solution B was added to solution A, and the mixture was heated to reflux and react for 1 h under a stream of nitrogen. The mixture was further heated to reflux for 1 h after adding 2,7-bis(4-bromophenyl)-9,9-dihexylfluorene (2.450 g, 3.80 mmol). After adding compound 10 (0.783 g, 1.087 mmol), the mixture was heated to reflux for 1 h, and further heated to reflux and react for 1.5 h after adding bromobenzene (0.85 g, 5.43 mmol). The reaction liquid was allowed to cool, and 100 ml of toluene was added. The reaction mixture was then dropped into an ethanol/water (500 ml/90 ml) solution to obtain a crude polymer.

The crude polymer was dissolved in toluene, and reprecipitated in acetone. The precipitated polymer was then filtered off. The resulting polymer was dissolved in toluene, washed with dilute hydrochloric acid, and reprecipitated in ammonia-containing ethanol. After filtration, the polymer was purified by column chromatography to obtain polymer 1 (4.3 g).

Weight-average molecular weight (Mw)=44,100
Number average molecular weight (Mn)=30,200
Degree of dispersion (Mw/Mn)=1.46

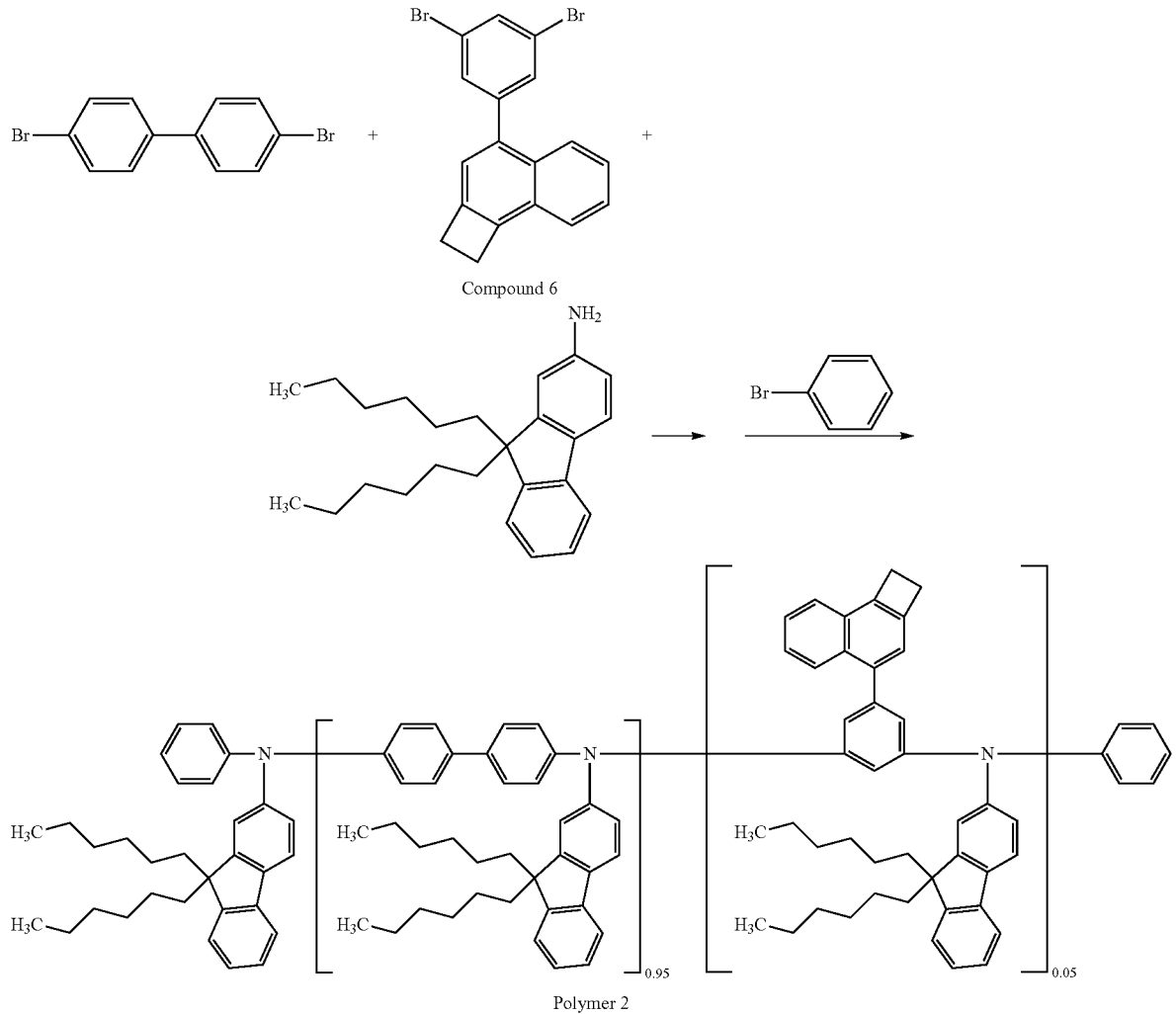

4,4'-Dibromobiphenyl (2.678 g, 8.58 mmol), 2-amino-9,9-dihexylfluorene (6.00 g, 17.17 mmol), tert-butoxysodium (5.53 g, 57.50 mmol), and toluene (90 ml) were charged into a system, and inside of the system was displaced with nitrogen before heating the mixture to 60° C. (solution A). [4-(N,N-Dimethylamino)phenyl]di-tert-butylphosphine (0.365 g, 1.376 mmol) was added to a 12-ml toluene solution of a tris(dibenzylideneacetone)dipalladium complex (0.158 g, 0.172 mmol), and the mixture was heated to 60° C. (solution B). Solution B was added to solution A, and the mixture was heated to reflux and react for 1.0 h under a stream of nitrogen. After adding compound 6 (0.333 g, 0.858 mmol), the mixture was heated to reflux for 30 min, and 4,4'-dibromobiphenyl (2.276 g, 7.294 mmol) was added. Bromobenzene (2.02 g, 12.87 mmol) was added after heating the mixture to reflux for 1.0 h, and the mixture was heated to reflux and react for 1.5 h. The reaction liquid was allowed to cool, and 100 ml of toluene was added. The reaction mixture was then dropped into an ethanol/water (500 ml/90 ml) solution to obtain a crude polymer.

The crude polymer was dissolved in toluene, and reprecipitated in acetone. The precipitated polymer was then filtered off. The resulting polymer was dissolved in toluene, washed with dilute hydrochloric acid, and reprecipitated in ammonia-containing ethanol. After filtration, the polymer was purified by column chromatography to obtain polymer 2 (0.7 g).

Weight-average molecular weight (Mw)=50,300
Number average molecular weight (Mn)=36,400
Degree of dispersion (Mw/Mn)=1.38

60° C. (solution B). Solution B was added to solution A, and the mixture was heated to reflux and react for 1 h under a stream of nitrogen. The mixture was further heated to reflux for 1 h after adding 4,4'-dibromobiphenyl (2.015 g, 6.46 mmol). After adding compound 10 (0.716 g, 0.994 mmol), the mixture was heated to reflux for 1 h, and further heated to reflux and react for 1.5 h after adding bromobenzene (1.26 g, 8.02 mmol). The reaction liquid was allowed to cool, and 100 ml of toluene was added. The reaction mixture was then dropped into an ethanol/water (500 ml/90 ml) solution to obtain a crude polymer.

The crude polymer was dissolved in toluene, and reprecipitated in acetone. The precipitated polymer was then

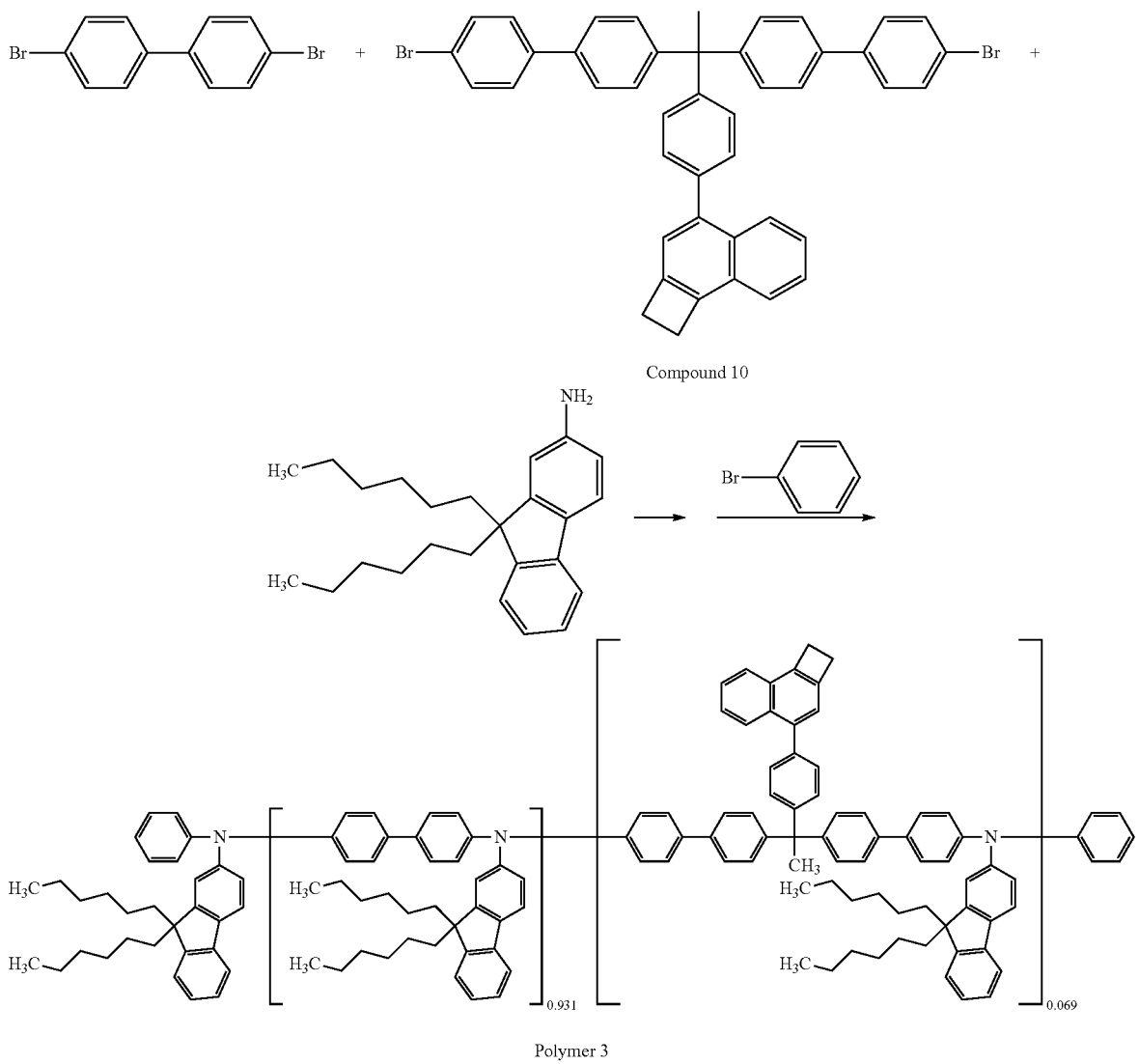

Polymer 3

4,4'-Dibromobiphenyl (2.500 g, 8.00 mmol), 2-amino-9,9-dihexylfluorene (5.60 g, 16.00 mmol), tert-butoxysodium (5.93 g, 61.8 mmol), and toluene (57.7 ml) were charged into a system, and inside of the system was displaced with nitrogen before heating the mixture to 60° C. (solution A). [4-(N,N-Dimethylamino)phenyl]di-tert-butylphosphine (0.340 g, 1.282 mmol) was added to a 9.5-ml toluene solution of a tris(dibenzylideneacetone)dipalladium complex (0.147 g, 0.160 mmol), and the mixture was heated to filtered off. The resulting polymer was dissolved in toluene, washed with dilute hydrochloric acid, and reprecipitated in ammonia-containing ethanol. After filtration, the polymer was purified by column chromatography to obtain polymer 3 (1.1 g).

Weight-average molecular weight (Mw)=37,100
Number average molecular weight (Mn)=27,700
Degree of dispersion (Mw/Mn)=1.34

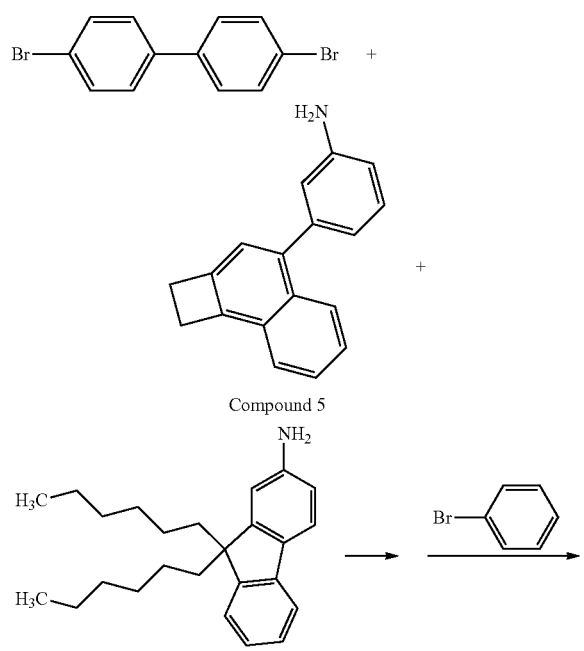

Compound 5

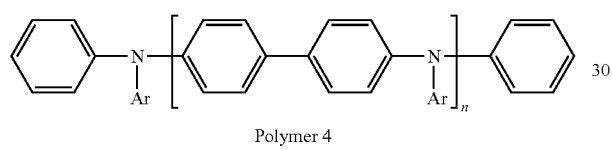

Polymer 4

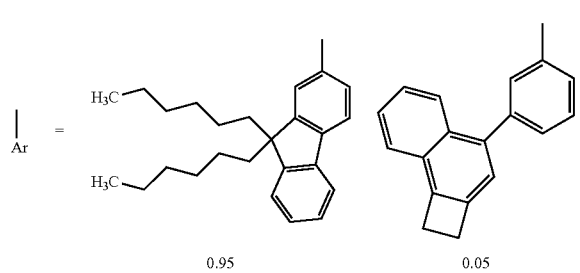

4,4'-Dibromobiphenyl (3.83 g, 12.22 mmol), compound 5 (0.299 g, 1.22 mmol), 2-amino-9,9-dihexylfluorene (8.10 g, 23.18 mmol), tert-butoxysodium (7.86 g, 81.74 mmol), and 120 ml of toluene were charged into a system, and inside of the system was displaced with nitrogen before heating the mixture to 60° C. (solution A). [4-(N,N-Dimethylamino) phenyl]di-tert-butylphosphine (0.518 g, 1.95 mmol) was added to a 15-ml toluene solution of a tris(dibenzylideneacetone)dipalladium complex (0.22 g, 0.244 mmol), and the mixture was heated to 60° C. (solution B). Solution B was added to solution A, and the mixture was heated to reflux and react for 1.0 h under a stream of nitrogen, followed by addition of 1,4-dibromobiphenyl (2.66 g, 8.54 mmol). 4,4'-Dibromobiphenyl (0.88 g, 2.83 mmol) was then added after heating the mixture to reflux for 1.0 h. Bromobenzene (2.88 g, 18.34 mmol) was added after heating the mixture to reflux for 1.0 h. The mixture was heated to reflux and react for 1.5 h, and the reaction liquid was allowed to cool. After adding 150 ml of toluene, the mixture was dropped into an ethanol/water (500 ml/90 ml) solution to obtain a crude polymer.

The crude polymer was dissolved in toluene, and reprecipitated in acetone. The precipitated polymer was then filtered off. The resulting polymer was dissolved in toluene, washed with dilute hydrochloric acid, and reprecipitated in ammonia-containing ethanol. After filtration, the polymer was purified by column chromatography to obtain polymer 4 (4.1 g).

Weight-average molecular weight (Mw)=46,700
Number average molecular weight (Mn)=33,800
Degree of dispersion (Mw/Mn)=1.38

[Insolubilization Rate Measurement]

Example 1

Thicknesses L1 and L2 were measured using the following method, and the L2/L1 ratio was calculated as insolubilization rate.

<Deposition Method, and Thickness L1 Measurement Method>

A 4 mass % cyclohexylbenzene solution of polymer 1 (Mw=44100, Mn=30200, Mw/Mn=1.46; composition) was prepared, and the composition was spin coated on a glass substrate to form a film.

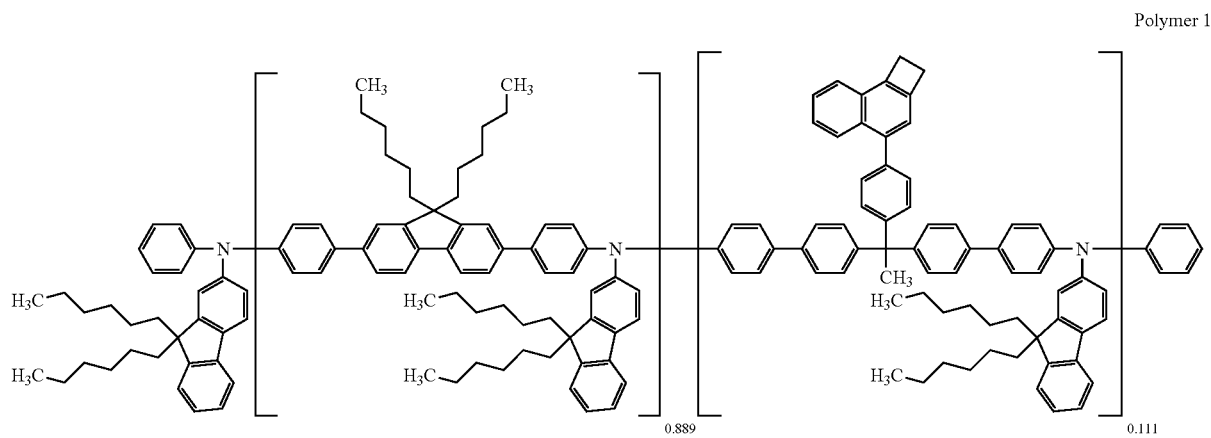

Polymer 1

Spin coating was performed in nitrogen at a spinner rotation speed of 2,400 rpm for 120 s. After the spin coating, the film was dried in nitrogen for 10 min on a hot plate at 210° C. A portion of the resulting film was scraped off, and the thickness L1 (nm) was measured with a step gauge (Tencor P-15).

<Thickness L2 Measurement Method>

The substrate after the thickness L1 measurement was set on a spinner, and cyclohexylbenzene was dropped on the portion where the thickness measurement was made. The substrate was then rotated after being allowed to stand for 30 s. In order to evaporate the cyclohexylbenzene, the substrate was baked on a hot plate, and the thickness L2 (nm) was measured at the same portion. The insolubilization rate L2/L1 after the cyclohexylbenzene spinning process was then calculated.

The thicknesses L1 and L2 were 58.0 nm and 49.9 nm, respectively, and the polymer 1 had an insolubilization rate of 86%.

Example 2

The insolubilization rate of polymer 2 (Mw=50,300, Mn=36,400, Mw/Mn=1.38) was measured in the same manner as in Example 1.

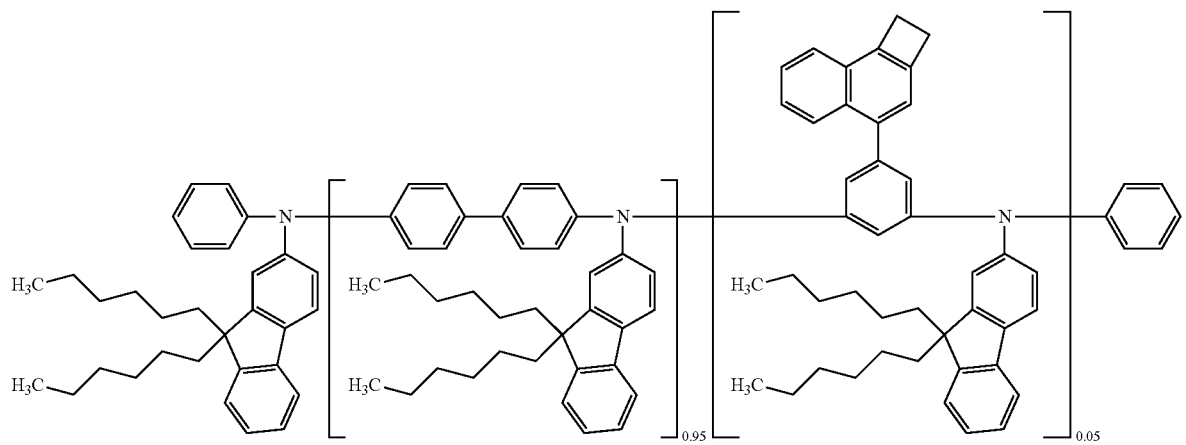

Polymer 2

The thicknesses L1 and L2 were 51.2 nm and 41.5 nm, respectively, and the polymer 2 had an insolubilization rate of 81%.

Example 3

The insolubilization rate of polymer 3 (Mw=37,100, Mn=27,700, Mw/Mn=1.34) was measured in the same manner as in Example 1.

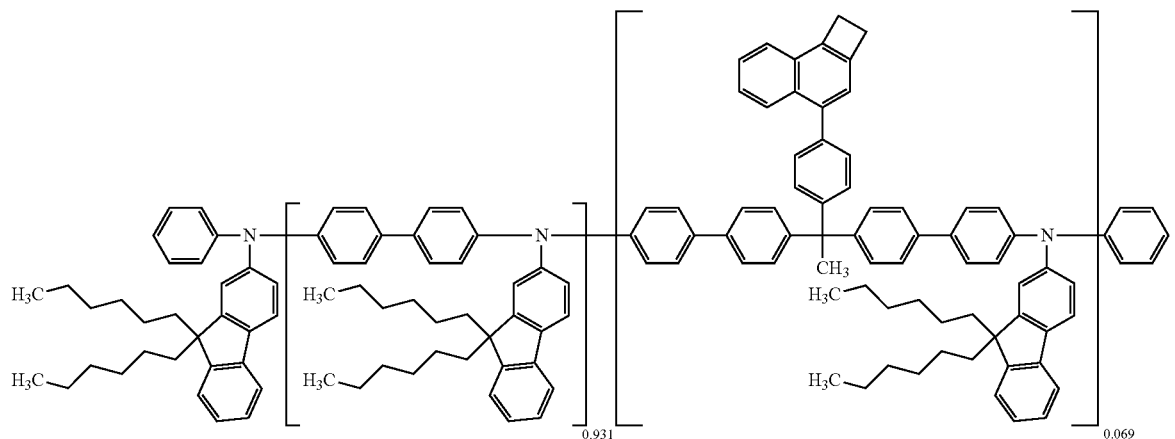

Polymer 3

The thicknesses L1 and L2 were 50.7 nm and 46.6 nm, respectively, and the polymer 3 had an insolubilization rate of 92%.

Example 4

The insolubilization rate of polymer 4 (Mw=46,700, Mn=33,800, Mw/Mn=1.38) was measured in the same manner as in Example 1.

Polymer 4

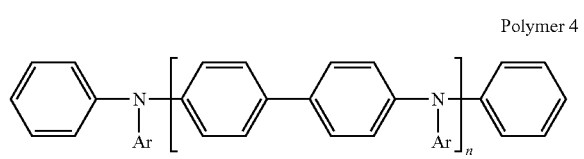

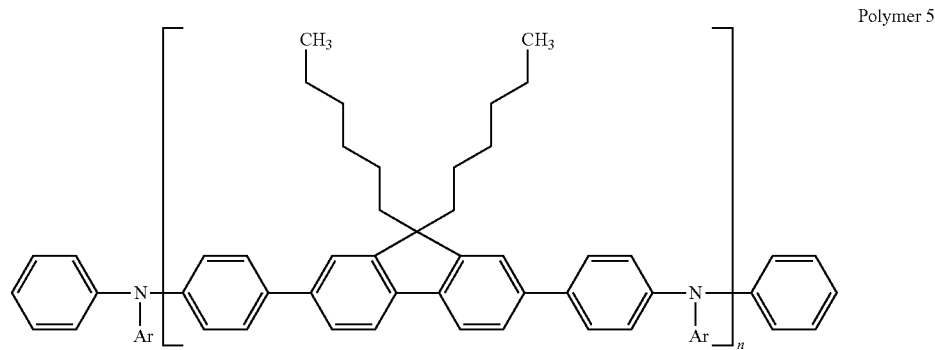

The thicknesses L1 and L2 were 52.2 nm and 48.6 nm, respectively, and the polymer 4 had an insolubilization rate of 93%.

Comparative Example 1

The insolubilization rate of polymer 5 (Mw=50,000, Mn=33,300, Mw/Mn=1.50) was measured in the same manner as in Example 1.

Polymer 5

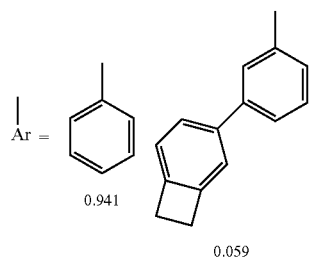

The thicknesses L1 and L2 were 78.8 nm and 0 nm, respectively, and the polymer 5 had an insolubilization rate of 0%.

Comparative Example 2

The insolubilization rate of polymer 6 (Mw=38,900, Mn=27,600, Mw/Mn=1.41) was measured in the same manner as in Example 1.

Polymer 6

The thicknesses L1 and L2 were 50.4 nm and 0 nm, respectively, and the polymer 6 had an insolubilization rate of 0%.

Comparative Example 3

The insolubilization rate of polymer 7 (Mw=48,000, Mn=33,100, Mw/Mn=1.45) was measured in the same manner as in Example 1.

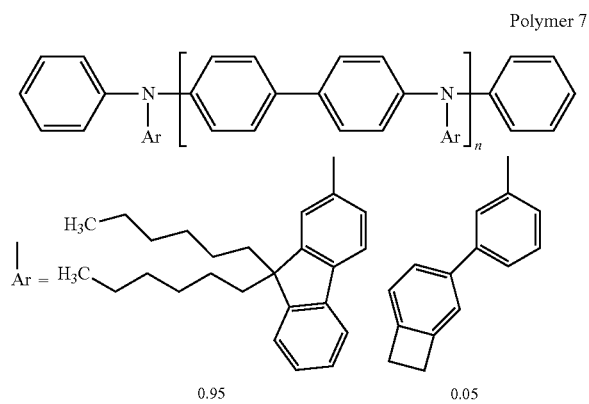

Polymer 7

The thicknesses L1 and L2 were 52.6 nm and 0 nm, respectively, and the polymer 7 had an insolubilization rate of 0%.

The insolubilization rate measurement results for Examples 1 to 4, and Comparative Examples 1 to 3 are summarized in Table 1.

TABLE 1

| | Sample | Insolubilization rate (%) | L1 (nm) | L2 (nm) |
|---|---|---|---|---|
| Ex. 1 | Polymer 1 | 86 | 58.0 | 49.9 |
| Ex. 2 | Polymer 2 | 81 | 51.2 | 41.5 |
| Ex. 3 | Polymer 3 | 92 | 50.7 | 46.6 |
| Ex. 4 | Polymer 4 | 93 | 52.2 | 48.6 |
| Com. Ex. 1 | Polymer 5 | 0 | 78.8 | 0 |
| Com. Ex. 2 | Polymer 6 | 0 | 50.4 | 0 |
| Com. Ex. 3 | Polymer 7 | 0 | 52.6 | 0 |

As shown in Table 1, the polymers of the present application containing 1,2-cyclobuta[a]naphthalene as a crosslinkable group were insolubilized, whereas no insolubilization occurred in the conventional polymers that had benzocyclobutene as a crosslinkable group.

[Organic Electroluminescent Element]

Example 5

The organic electroluminescent element shown in the FIGURE was produced.

A glass substrate 1 that had had an indium tinoxide (ITO) transparent conductive film deposited thereon by sputtering was patterned into 2 mm-wide stripes by using a common photolithography technique and hydrochloric acid etching to form an anode 2 having a thickness of 70 nm. The ITO substrate with the formed patterns was then subjected to a series of washing procedures, starting from ultrasonic washing with a surfactant aqueous solution, and then to water washing with ultrapure water, ultrasonic washing with ultrapure water, and water washing with ultrapure water. The substrate was dried with compressed air, and then subjected to ultraviolet ozone washing.

Thereafter, a coating liquid for forming a hole injection layer was prepared that contained the polymer 7, 4-isopropyl-4'-methyldiphenyliodonium tetrakis(pentafluorophenyl) borate represented by structural formula (A1), and ethyl benzoate. The coating liquid was deposited on the anode 2 by spin coating, and heated under the conditions below to obtain a hole injection layer having a thickness of 40 nm.

(A1)

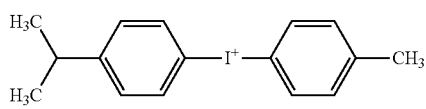

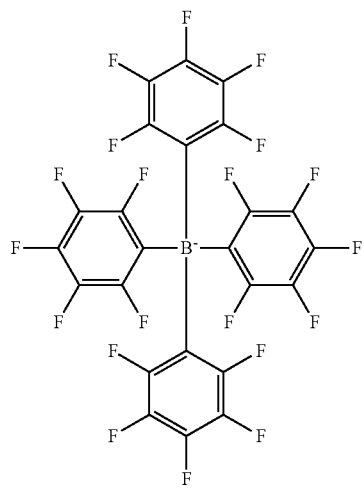

<Coating Liquid for Forming Hole Injection Layer>

Solvent: ethyl benzoate

Coating liquid concentration:

Polymer 7: 2.5 mass %

A1: 0.5 mass %

<Deposition Conditions for Hole Injection Layer 3>

Spin coating atmosphere: atmosphere

Heating conditions: 240° C. for 10 min in the atmosphere

A coating liquid for forming a hole transport layer containing the polymer 1 was prepared. The coating liquid was deposited on the hole injection layer 3 by spin coating under the conditions below, and heated to obtain a hole transport layer having a thickness of 40 nm.

Polymer 1

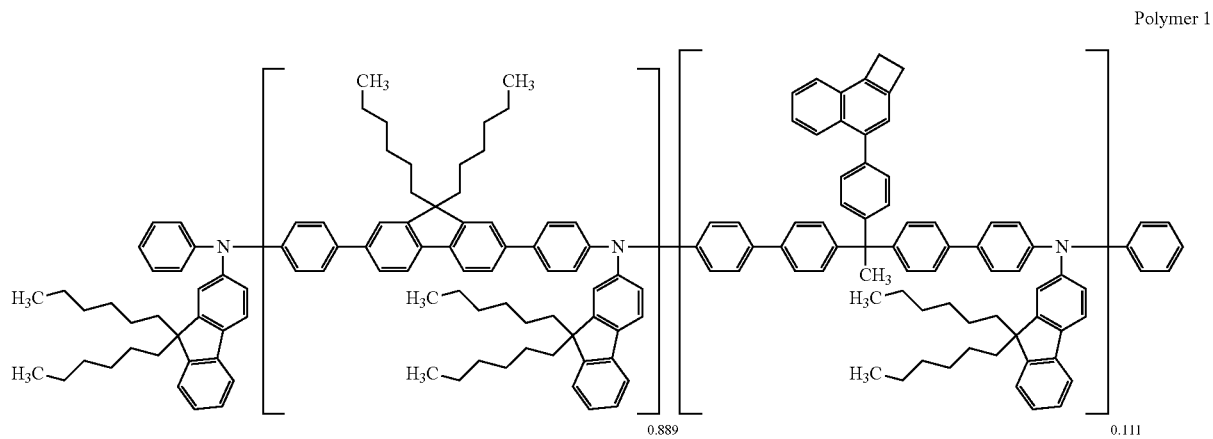

<Coating Liquid for Forming Hole Transport Layer>
Solvent: cyclohexylbenzene
Coating liquid concentration: 1.5 mass %
<Deposition Conditions for Hole Transport Layer 4>
Spin coating atmosphere: Nitrogen atmosphere
Heating conditions: 220° C. for 10 min in nitrogen
A coating liquid for forming a light-emitting layer containing compounds (H1), (H2), and (D1) of the following structural formulae was prepared. The coating liquid was deposited by spin coating under the conditions below, and heated to form a light-emitting layer, 50-nm thick, on the hole transport layer 4.

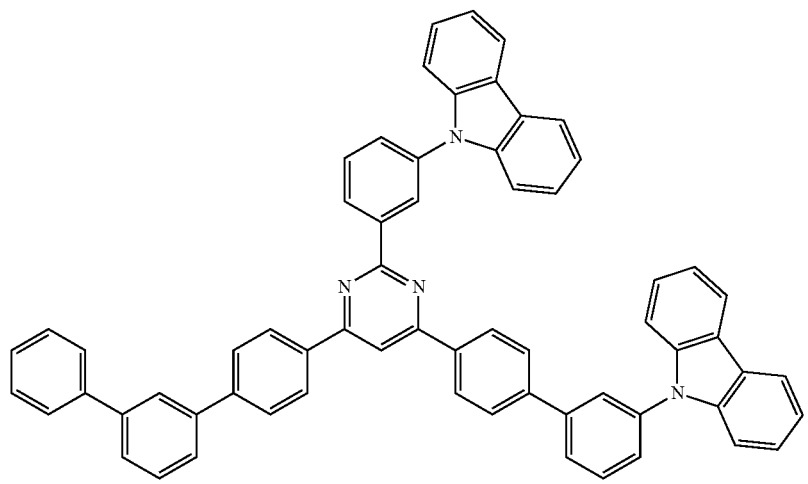

(H1)

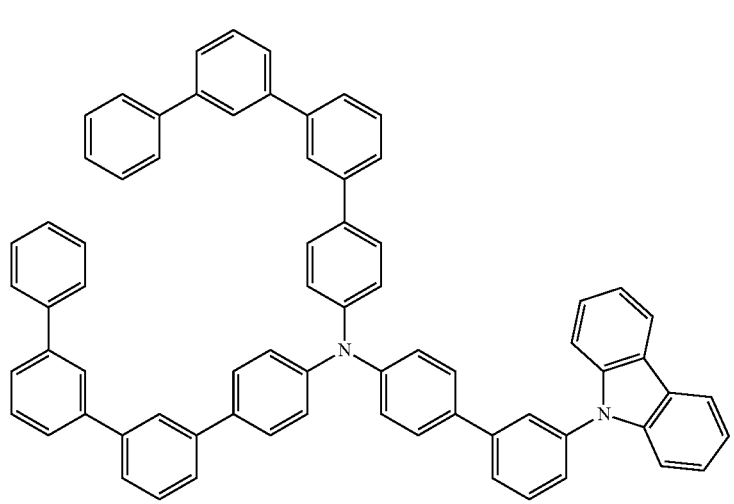

(H2)

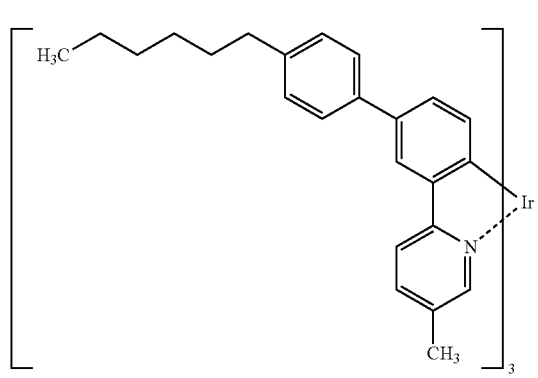

(D1)

<Coating Liquid for Forming Light-Emitting Layer>
 Solvent: cyclohexylbenzene
 Coating liquid concentration:
 H1: 1.2 mass %
 H2: 3.6 mass %
 D1: 0.48 mass %

<Deposition Conditions for Light-Emitting Layer 5>
 Spin coating atmosphere: nitrogen atmosphere
 Heating conditions: 130° C. for 10 min in nitrogen The substrate with the deposited layers including the light-emitting layer was transferred into a vacuum vapor deposition apparatus, and an organic compound (E1) of the following structure was laminated on the light-emitting layer 5 by using a vacuum vapor deposition method to form a hole blocking layer 6 having a thickness of 15 nm.

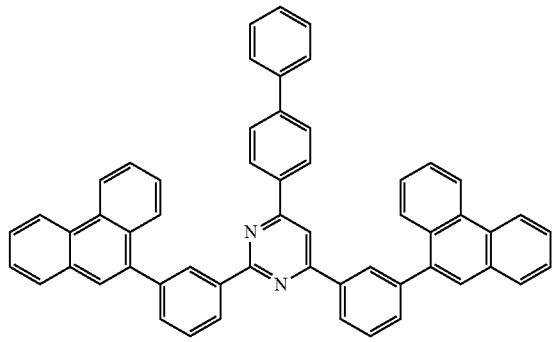

(E1)

Thereafter, the organic compound (E2) of the following structure was laminated on the hole blocking layer 6 by using a vacuum vapor deposition method to form an electron transport layer 7 having a thickness of 20 nm.

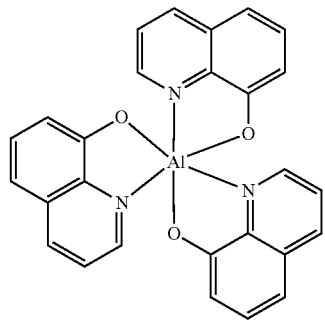

(E2)

The element after the vapor deposition of the layers including the electron transport layer 7 was transferred to a separate vacuum vapor deposition apparatus, and a 2 mm-wide stripe shadow mask, serving as a vapor deposition mask for cathode, was attached to the element in such a manner that the stripes were orthogonal to the ITO stripes of the anode 2. The electron injection layer 8 was deposited by depositing lithium fluoride (LiF) on the electron transport layer 7 in a thickness of 0.5 nm by using a vacuum vapor deposition method with a molybdenum board. The cathode 9 was formed by heating aluminum, and forming an 80 nm-thick aluminum layer using a vacuum vapor deposition method with a molybdenum board in the manner described above. The substrate temperature was maintained at room temperature during the vapor deposition of these two layers.

In order to prevent deterioration of the element due to moisture or the like in the atmosphere during storage, a sealing process was performed according to the following method.

A light-curable resin (a 30Y-437 manufactured by Three-Bond Fine Chemical Co., Ltd.) was applied in a band of about 1-mm width at the peripheries of a 23 mm×23 mm glass plate in a nitrogen glove box, and a moisture getter sheet (manufactured by Dynic) was installed at the central portion. The substrate after the formation of the cathode was then mated with the glass plate with the vapor deposited surface facing the desiccant sheet. Thereafter, the resin was cured by applying ultraviolet light to only the region where the light-curable resin was applied.

This completed an organic electroluminescent element that had an emission area measuring 2 mm×2 mm in size. The properties of this element are shown in Table 2.

Comparative Example 4

An organic electroluminescent element was produced in the same manner as in Example 5, except that the hole transport layer 4 was formed by spin coating and heating a coating liquid for forming a hole transport layer that contained the polymer 5. The properties of this element are shown in Table 2.

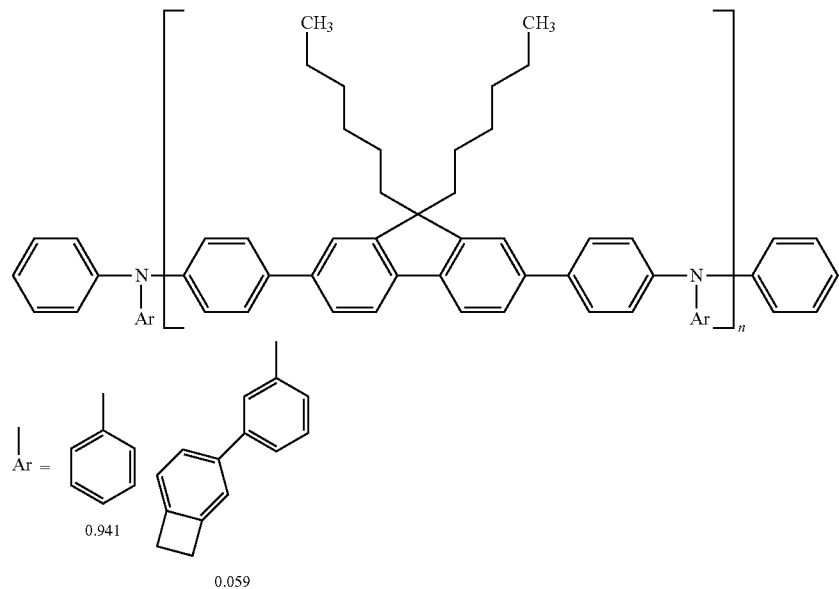

Polymer 5

<Coating Liquid for Forming Hole Transport Layer>
  Solvent: cyclohexylbenzene
  Coating liquid concentration: 1.5 mass %
<Deposition Conditions for Hole Transport Layer 4>
  Spin coating atmosphere: nitrogen atmosphere
  Heating conditions: 220° C. for 10 min in nitrogen

TABLE 2

|  | Hole transport layer | Voltage (V) at 1 cd/m$^2$ | Voltage (V) at 100 cd/m$^2$ |
|---|---|---|---|
| Ex. 5 | Polymer 1 | 3.4 | 4.8 |
| Com. Ex. 4 | Polymer 5 | 4.2 | 9.0 |

As is clear from Table 2, the organic electroluminescent element using the polymer of the present invention had lower voltages.

Example 6

A coating liquid for forming a hole injection layer was prepared under the conditions below. The coating liquid contained the polymer 2, 4-isopropyl-4'-methyldiphenyliodonium tetrakis(pentafluorophenyl)borate represented by the formula (A1), and ethyl benzoate. An organic electroluminescent element was produced in the same manner as in Example 5, except that a hole injection layer having a thickness of 40 nm was formed by depositing the coating liquid on the anode 2 by spin coating, and heating the coating under the conditions below. The properties of this element are shown in Table 3.

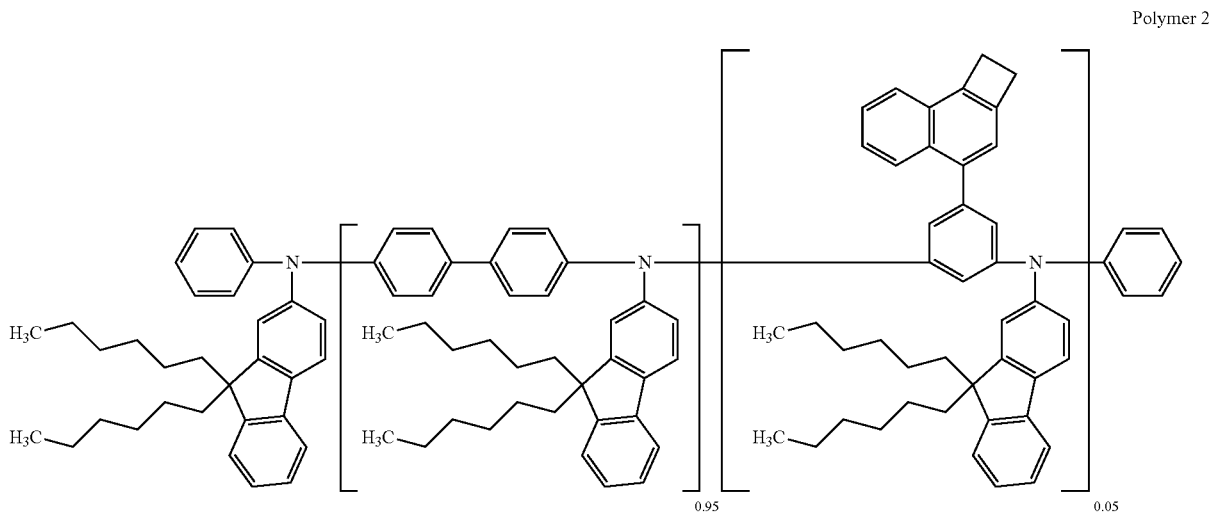

Polymer 2

<Coating Liquid for Forming Hole Injection Layer>
  Solvent: ethyl benzoate
  Coating liquid concentration:
    Polymer 2: 2.5 mass %
    A1: 0.5 mass %
<Deposition Conditions for Hole Injection Layer 3>
  Spin coating atmosphere: atmosphere
  Heating conditions: 220° C. for 10 min in the atmosphere Example 7

An organic electroluminescent element was produced in the same manner as in Example 6, except that the polymer 2 used for the coating liquid for forming a hole injection layer was replaced with polymer 3. The properties of this element are shown in Table 3.

Polymer 3

Example 8

An organic electroluminescent element was produced in the same manner as in Example 6, except that the polymer 2 used for the coating liquid for forming a hole injection layer was replaced with polymer 4. The properties of this element are shown in Table 3.

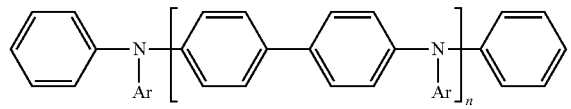

Polymer 4

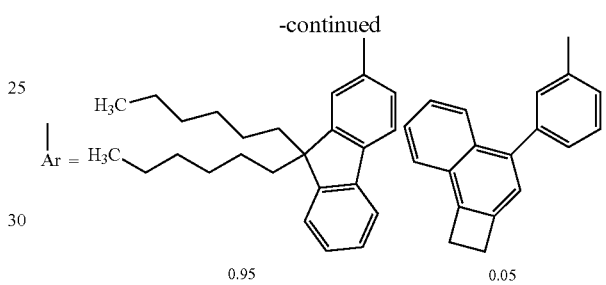

-continued

Comparative Example 5

An organic electroluminescent element was produced in the same manner as in Example 6, except that the polymer 2 used for the coating liquid for forming a hole injection layer was replaced with polymer 7, and that the polymer 1 used for the coating liquid for forming a hole transport layer was replaced with polymer 5. The properties of this element are shown in Table 3.

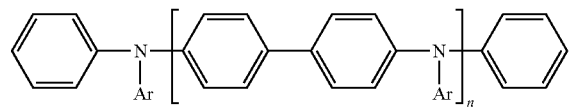

Polymer 7

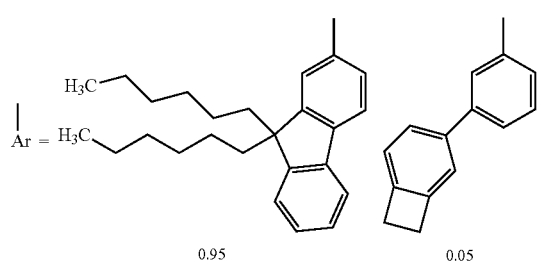

-continued

Polymer 5

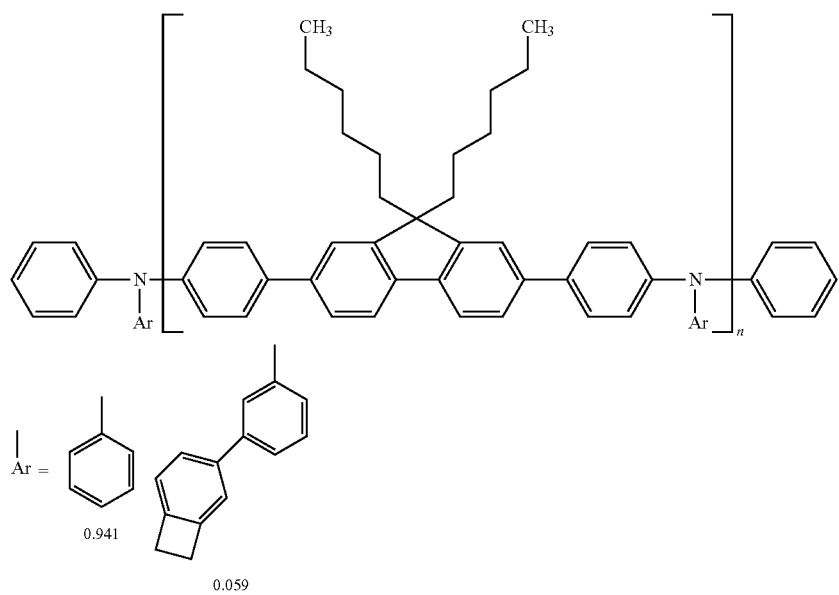

TABLE 3

| | Hole injection layer | Hole transport layer | Voltage (V) at 1 cd/m² | Voltage (V) at 100 cd/m² |
|---|---|---|---|---|
| Ex. 6 | Polymer 2 | Polymer 1 | 3.4 | 4.7 |
| Ex. 7 | Polymer 3 | Polymer 1 | 3.4 | 4.8 |
| Ex. 8 | Polymer 4 | Polymer 1 | 3.4 | 4.7 |
| Com. Ex. 5 | Polymer 7 | Polymer 5 | 4.1 | 8.7 |

As is clear from Table 3, the organic electroluminescent elements using the polymers of the present invention had lower voltages.

While the present invention has been described in detail and with reference to certain embodiments of the invention, it will be apparent to a skilled person that various changes and modifications may be made thereto without departing from the spirit and scope of the invention. The present application is based on Japanese Patent Application No. 2014-040769 filed Mar. 3, 2014, the contents of which are herein incorporated by reference.

INDUSTRIAL APPLICABILITY

The polymer of the present invention has excellent electrochemical stability, and elements containing layers formed by using the polymer have potential application in flat panel displays (for example, flat panel display for OA computers, and wall-mounted televisions), in-vehicle display devices, cell phone displays, light sources featuring surface-emission (for example, light sources for copiers, and light sources for backlights of liquid crystal displays and instruments), display boards, and sign lamps. The polymer of the present invention thus has a great technical value.

The invention claimed is:

1. A polymer having a crosslinkable group represented by the following formula (1):

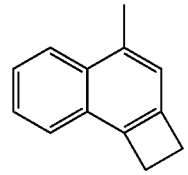

(1)

wherein the 1,2-dihydrocyclobuta[a]naphthalene ring may have a substituent.

2. The polymer according to claim 1, which comprises a repeating unit represented by the following formula (2):

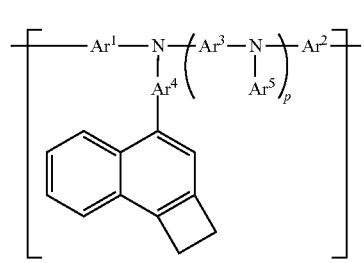

(2)

wherein p represents an integer of 0 to 3,

Ar¹ and Ar² each independently represent a direct bond, an aromatic hydrocarbon group that may have a substituent, or an aromatic heterocyclic group that may have a substituent, Ar³ to Ar⁵ each independently represent an aromatic hydrocarbon group that may have a substituent, or an aromatic heterocyclic group that may have a substituent, and the Ar¹ and Ar² are not direct bonds at the same time.

3. The polymer according to claim 1, which comprises a repeating unit represented by the following formula (3):

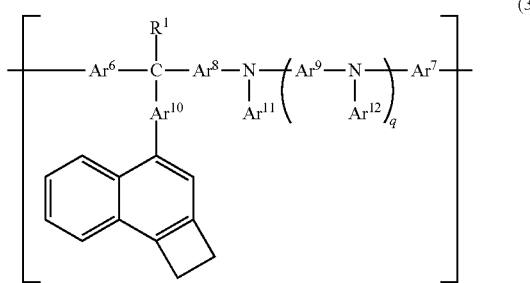

(3)

wherein q represents an integer of 0 to 3,
$R^1$ represents an alkyl group of 1 to 24 carbon atoms that may have a substituent, an aromatic hydrocarbon group that may have a substituent, or an aromatic heterocyclic group that may have a substituent,
$Ar^6$ and $Ar^7$ each independently represents a direct bond, an aromatic hydrocarbon group that may have a substituent, or an aromatic heterocyclic group that may have a substituent,
$Ar^8$ to $Ar^{12}$ each independently represents an aromatic hydrocarbon group that may have a substituent, or an aromatic heterocyclic group that may have a substituent, and
the $Ar^6$ and $Ar^7$ are not direct bonds at the same time.

4. The polymer according to claim 1, which comprises a repeating unit represented by the following formula (4):

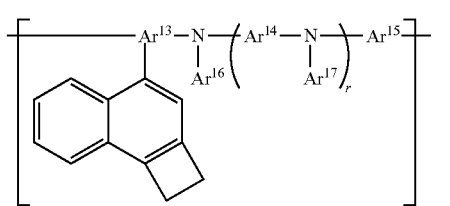

(4)

wherein r represents an integer of 0 to 3,
$Ar^{13}$, $Ar^{14}$, $Ar^{16}$, and $Ar^{17}$ each independently represent an aromatic hydrocarbon group that may have a substituent, or an aromatic heterocyclic group that may have a substituent, and $Ar^{15}$ represents a direct bond, an aromatic hydrocarbon group that may have a substituent, or an aromatic heterocyclic group that may have a substituent.

5. The polymer according to claim 1, which has a weight-average molecular weight (Mw) of 20,000 or more, and a degree of dispersion (Mw/Mn) of 2.5 or less.

6. A composition for organic electroluminescent element, which comprises the polymer of claim 1.

7. An organic electroluminescent element comprising a substrate, an anode and a cathode provided on the substrate, and an organic layer provided between the anode and the cathode, wherein the organic layer contains a layer formed by a wet film formation method using the composition for organic electroluminescent elements of claim 6.

8. The organic electroluminescent element according to claim 7, wherein the layer formed by a wet film formation method is at least one of a hole injection layer and a hole transport layer.

9. The organic electroluminescent element according to claim 7, which comprises a hole injection layer, a hole transport layer and a light-emitting layer between the anode and the cathode, wherein the hole injection layer, the hole transport layer, and the light-emitting layer are all formed by a wet film formation method.

10. An organic EL display device comprising the organic electroluminescent element of claim 7.

11. An organic EL lighting device comprising the organic electroluminescent element of claim 7.

12. A compound represented by the following formula (5):

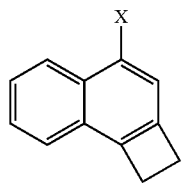

(5)

wherein X represents a halogen atom.

* * * * *